(12) United States Patent
Asaka et al.

(10) Patent No.: US 9,883,825 B2
(45) Date of Patent: Feb. 6, 2018

(54) LIVING BODY OPTICAL MEASUREMENT APPARATUS, LIVING BODY OPTICAL MEASUREMENT METHOD, AND ENGAGEMENT MEMBER FOR MOBILE POSITION SENSOR

(71) Applicant: HITACHI MEDICAL CORPORATION, Tokyo (JP)

(72) Inventors: Hirokazu Asaka, Tokyo (JP); Takashi Ishizuka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 388 days.

(21) Appl. No.: 14/382,514

(22) PCT Filed: Mar. 26, 2013

(86) PCT No.: PCT/JP2013/058673
§ 371 (c)(1),
(2) Date: Sep. 2, 2014

(87) PCT Pub. No.: WO2013/146725
PCT Pub. Date: Oct. 3, 2013

(65) Prior Publication Data
US 2015/0038811 A1    Feb. 5, 2015

(30) Foreign Application Priority Data
Mar. 29, 2012  (JP) ................................ 2012-077278

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0042* (2013.01); *A61B 5/0073* (2013.01);
(Continued)

(58) Field of Classification Search
None
See application file for complete search history.

(56) References Cited

U.S. PATENT DOCUMENTS

| 6,542,763 B1 | 4/2003 | Yamashita et al. |
| 7,190,826 B2 | 3/2007 | Russell et al. |
| 2012/0203088 A1 | 8/2012 | Tanii et al. |

FOREIGN PATENT DOCUMENTS

| EP | 1 652 470 A1 | 5/2006 |
| JP | A-2004-357899 | 12/2004 |

(Continued)

OTHER PUBLICATIONS

Oct. 13, 2015 Extended Search Report issued in European Patent Application No. 13767849.6.
(Continued)

*Primary Examiner* — Eric Winakur
*Assistant Examiner* — Marjan Fardanesh
(74) *Attorney, Agent, or Firm* — Oliff PLC

(57) ABSTRACT

A living body optical measurement apparatus of the present invention includes: a light irradiation/measurement unit for irradiating light to an object and measuring the light passed through the object, a signal processing unit for processing measurement data of the light irradiation/measurement unit and creating a living body optical measurement image, and a position measurement unit for measuring positions where light is irradiated to an object and where the passing light is extracted from the object, the light irradiation/measurement unit includes plural optical fibers. The light irradiation/measurement unit includes plural optical fibers, plural optical fiber plugs attached to the plural optical fibers respectively, and a holder fixed detachably at a measurement site of an object and holds the plural optical fiber plugs. The position measurement unit includes a mobile position sensor and an engaging member having a shape detachably (Continued)

engaged with the plural optical fiber plugs attached to the mobile position sensor and held in the holder.

14 Claims, 30 Drawing Sheets

(51) Int. Cl.
    *A61B 5/02*        (2006.01)
    *A61B 5/026*      (2006.01)
    *A61B 5/0295*     (2006.01)
    *A61B 5/06*        (2006.01)
    *A61B 5/0205*     (2006.01)
    *A61B 5/145*      (2006.01)
    *A61B 5/024*      (2006.01)

(52) U.S. Cl.
    CPC ........ *A61B 5/02028* (2013.01); *A61B 5/0261* (2013.01); *A61B 5/0295* (2013.01); *A61B 5/062* (2013.01); *A61B 5/14553* (2013.01); *A61B 5/4064* (2013.01); *A61B 5/0205* (2013.01); *A61B 5/02416* (2013.01); *A61B 5/1455* (2013.01); *A61B 5/14546* (2013.01); *A61B 5/6803* (2013.01); *A61B 5/6814* (2013.01); *A61B 5/6844* (2013.01); *A61B 2560/0418* (2013.01); *A61B 2562/0233* (2013.01); *A61B 2562/223* (2013.01); *A61B 2562/228* (2013.01)

(56) References Cited

FOREIGN PATENT DOCUMENTS

| JP | 2009261588 A | 11/2009 |
|---|---|---|
| JP | A-2011-050504 | 3/2011 |
| WO | 2009/134674 A1 | 11/2009 |
| WO | WO 2011/046072 A1 | 4/2011 |

OTHER PUBLICATIONS

International Search Report issued in International Application No. PCT/JP2013/058673 dated May 21, 2013.

FIG.11
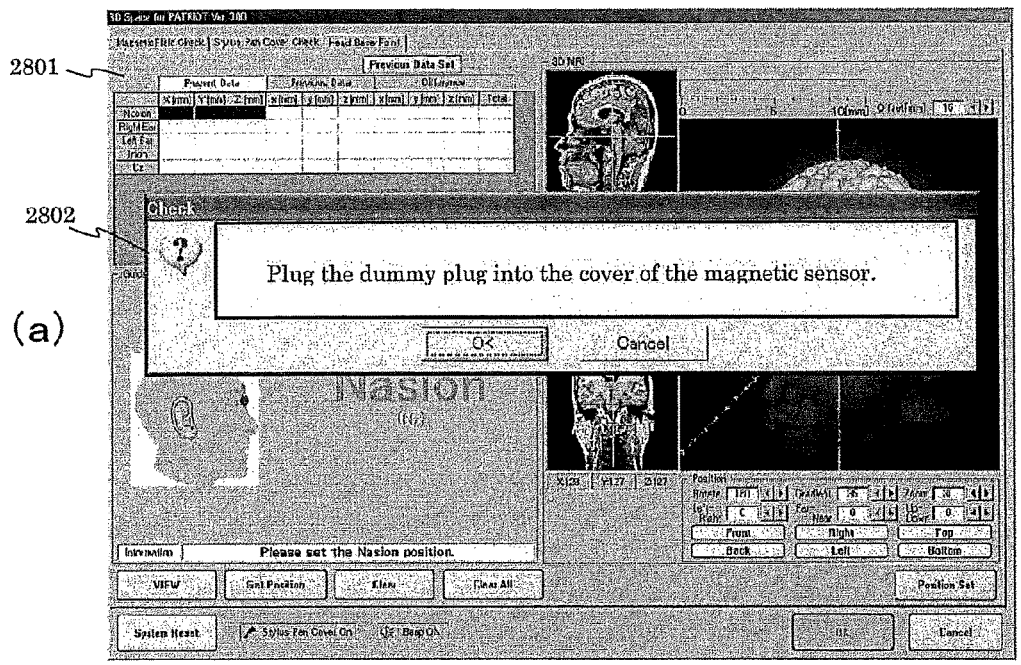
(a)
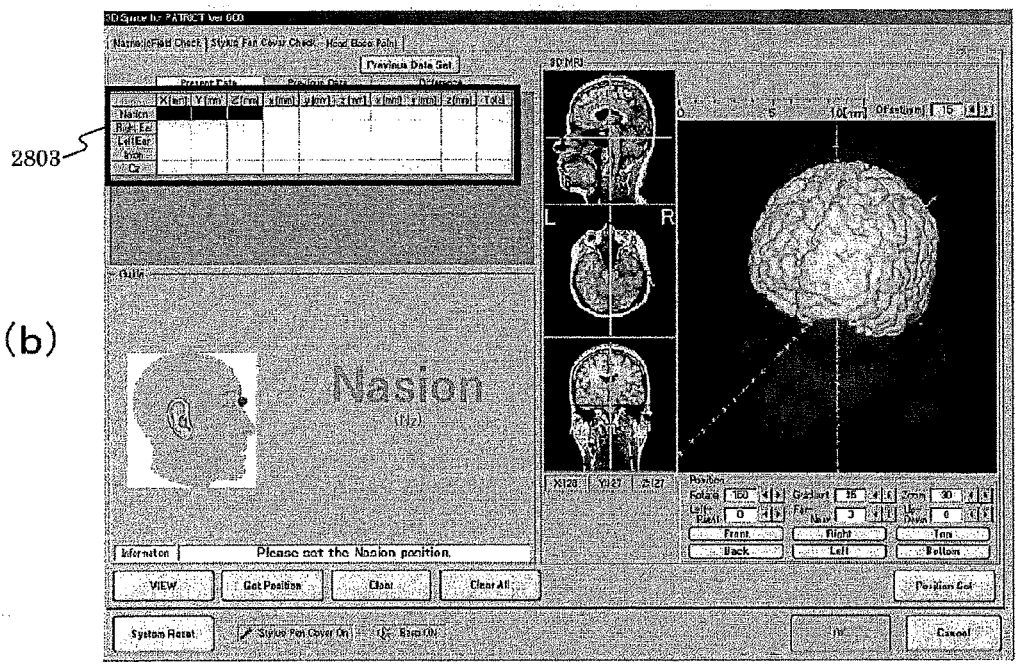
(b)

FIG.12
(a)
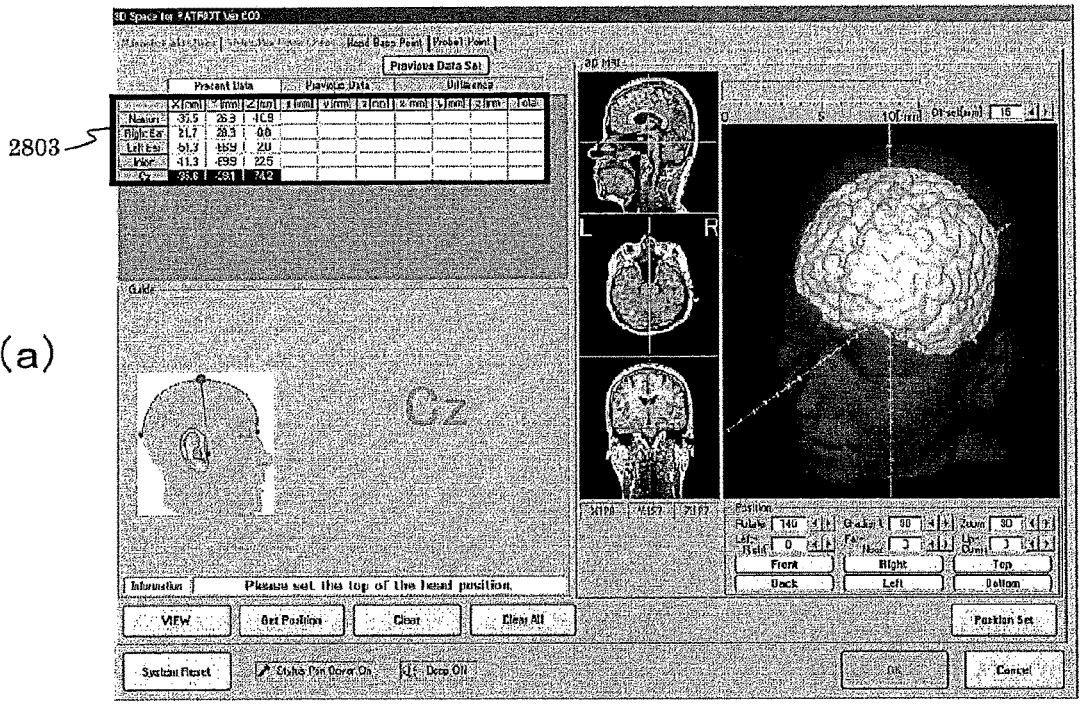
(b)
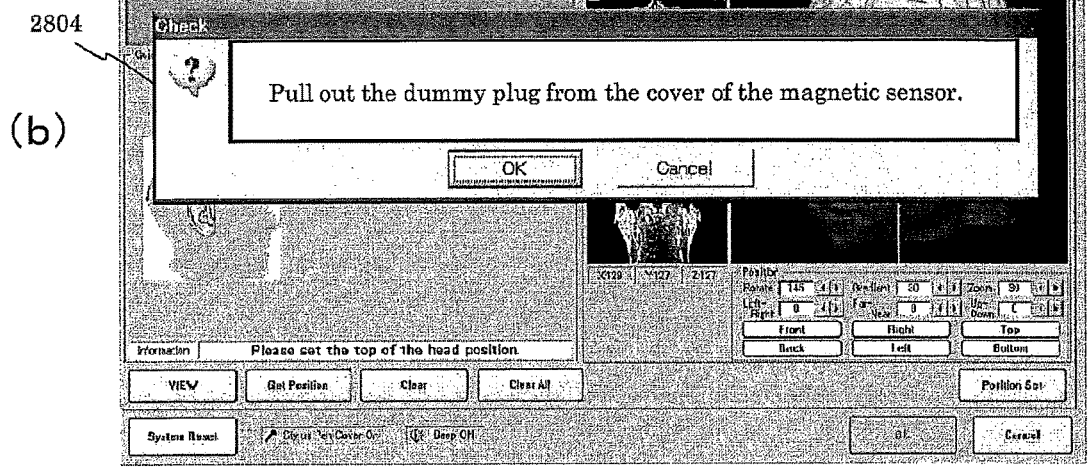

FIG.28
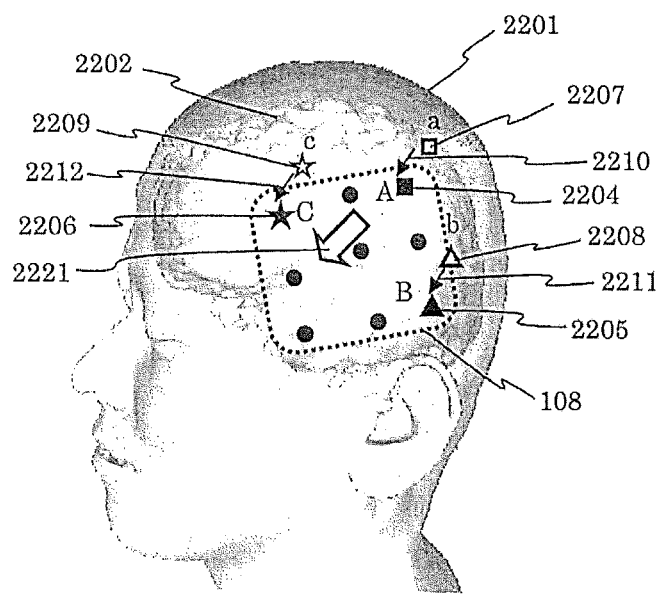
$$\frac{|A-a|+|B-b|+|C-c|}{3}$$ ── 2213
$|A-a|$ ── 2214
$|B-b|$ ── 2215
$|C-c|$ ── 2216
$$\frac{|A-a|+|B-b|+|C-c|}{3}$$ ── 2217
$|A-a|$ ── 2218
$|B-b|$ ── 2219
$|C-c|$ ── 2220

LIVING BODY OPTICAL MEASUREMENT APPARATUS, LIVING BODY OPTICAL MEASUREMENT METHOD, AND ENGAGEMENT MEMBER FOR MOBILE POSITION SENSOR

TECHNICAL FIELD

The present invention relates to a living body optical measurement apparatus that measures blood circulation, hemodynamics, and hemoglobin quantity change inside a living body by irradiating near-infrared light to a living body and measuring light that passed through the inside of a living body or that reflected inside a living body.

BACKGROUND ART

The living body optical measurement apparatus is an apparatus that irradiates light in a range from a visible wavelength to a near-infrared wavelength from a optical fiber to a living body through a scalp to measure the light that passed through the inside of a living body or that reflected inside a living body from the scalp. Recently, creating images of data measured by a multi-channel device has been achieved (for example, PTL 1).

In PTL 1, a living body optical measurement apparatus, which measures a light irradiation position and a light detection position for a measurement target using a mobile position sensor (pen-shaped magnetic sensor) and displays a living body passing light intensity image with it superimposed on a head surface image and a brain surface image of the measurement target, is disclosed.

CITATION LIST

Patent Literature

PTL 1: Japanese Unexamined Patent Application Publication No. 2011-046072

SUMMARY OF INVENTION

Technical Problem

However, in PTL 1, measurement is performed by inserting a mobile position sensor in a position where the tip of an optical fiber was after detaching the optical fiber from a probe holder once. Therefore, an operator presumes the original tip position before detaching the optical fiber for the measurement, which results in a technical problem where the tip position of the optical fiber cannot be measured accurately.

The purpose of the present invention is to measure a tip position of an optical fiber accurately with the tip of the optical fiber of the living body optical measurement apparatus in contact with an object.

Solution to Problem

In order to solve the problem, the present invention includes a light irradiation and measurement unit for irradiating light on an object and measuring the light passed through the object; a signal processing unit for processing data measured by the light irradiation and measurement unit to create living body optical measurement images; and a position measurement unit for measuring positions where the light irradiation and measurement unit irradiates light to the object and where the passing light from the object is extracted, the light irradiation and measurement unit is comprised of plural optical fibers; plural optical fiber plugs attached to the plural optical fibers respectively; and a holder that is detachably fixed at a measurement site of an object and holds the plural optical fiber plugs, and the position measurement unit is comprised of a mobile position sensor; and an engaging member having a shape which is detachably engaged with the plural optical fiber plugs that are attached to the mobile position sensor and held in the holder.

Advantageous Effects of Invention

As described above, according to the present invention, a position of the tip of an optical fiber can be measured without detaching the optical fiber and the optical fiber plug of a living body optical measurement apparatus from a holder in a state where the tip of the optical fiber comes in contact with an object.

BRIEF DESCRIPTION OF DRAWINGS

FIGS. 11(a) and 11(b) are explanatory diagrams showing screen examples that the signal processing unit 113 displays on the display device 114 in a living body optical measurement method.

FIGS. 12(a) and 12(b) are explanatory diagrams showing screen examples that the signal processing unit 113 displays on the display device 114 in a living body optical measurement method.

FIG. 28 is an explanatory diagram showing an image example to display error bars showing a shift amount and a moving direction so that positions of optical fibers in three locations correspond to the previous positions of the optical fibers at a time.

DESCRIPTION OF EMBODIMENTS

Figure 1:
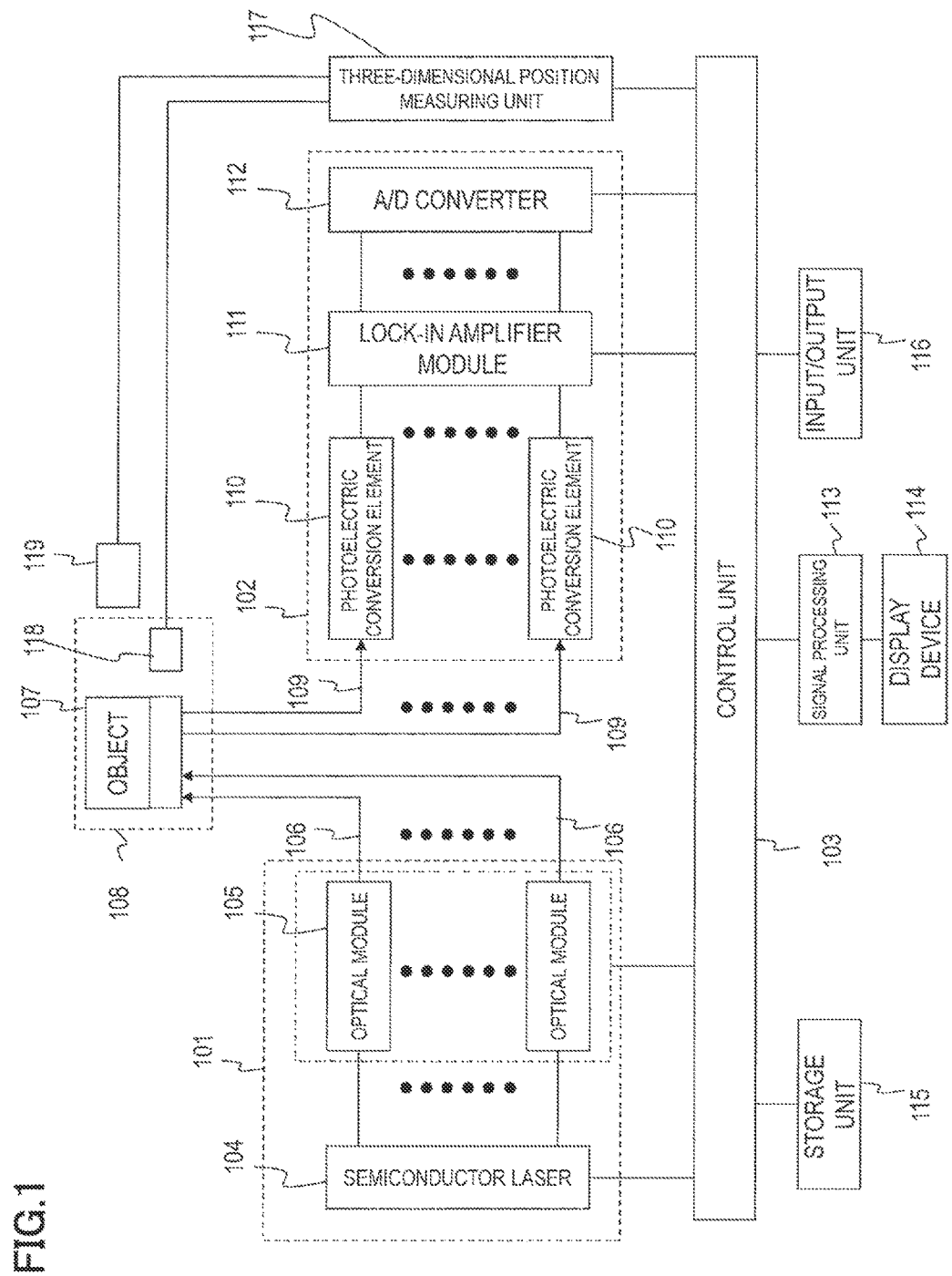
FIG. 1 is a block diagram showing an overall configuration of a living body optical measurement apparatus of the present invention.

A living body optical measurement apparatus of the present invention has a configuration including a light irradiation and measurement unit that irradiates light to an object and measures the light passed through the object, a signal processing unit that processes data measured by the light measurement unit to generate living body optical measurement images, a position measurement unit that measures positions where the light irradiation and measurement unit irradiates light to the object and where the passing light from the object is measured.

Here, a light irradiation and measurement unit is comprised of plural optical fibers, an optical fiber plug attached to the optical fibers, and a holder that is detachably fixed at a measurement site of an object and holds the plural optical fiber plugs.

A position measurement unit includes a mobile position sensor, an engaging member attached to the mobile position sensor, and a calculating unit.

An engaging member has a shape in a positional relationship (hereinafter, such positional relationship is referred to as a predetermined positional relationship) where an optical fiber plug held in a holder, a detection position of a mobile position sensor, a surface of a measurement site are engaged with each other detachably.

A calculating unit calculates a position detected by a mobile position sensor in a state where an optical fiber plug is engaged with an engaging member and a tip position of an optical fiber of the optical fiber plug from a predetermined positional relationship. Hence, a position of the tip section of an optical fiber can be measured without detaching the optical fiber and the optical fiber plug from a holder in a state where the tip of the optical fiber is in contact with an object.

If an optical fiber plug includes a fixing unit fixed by an optical fiber, an engaging member may have a structure where the tip of a mobile position sensor comes into contact with an end of the fixing unit when engaged with an optical fiber plug. As a specific example, a fixing unit is configured so that a tubular portion fixed to an optical fiber and a bar-shaped portion fixed at an end of the tubular portion, and a mobile position sensor is configured so that it comes into contact with the bar-shaped portion to detect the position.

For example, an engaging member is configured so that it has an opening with a shape that is engaged with the periphery of an optical fiber plug. As a specific example, the opening of the engaging member is created so that the depth direction is the same as the axial direction of a mobile position sensor to hold an optical fiber of an optical fiber plug inserted in the opening on the same axis as the axial direction of the mobile position sensor. In this case, a calculating unit can find a tip position of the optical fiber by calculating a position remote from the tip of the mobile position sensor by the predetermined distance in the axial direction.

An optical fiber plug may be configured so that a holding portion holding a fixing unit movably in the axial direction of the tip section of an optical fiber is included. In this case, a plurality of holes are provided on a holder to hold an optical fiber plug, the periphery of the holding portion of the optical fiber plug is engaged with the periphery of the holder holes, which can attach the optical fiber plug to the holder. Also, an optical fiber may be configured so that the periphery of the tip section is fixed at the fixing unit of the optical fiber plug, is bent inside the optical fiber plug, and then is pulled to the outside from a side surface of the optical fiber plug. In this case, it is desirable to provide a notch in which an optical fiber pulled out from the side surface of the optical fiber plug is inserted, on the opening edge of the engaging member.

By attaching a pseudo plug to an engaging member in a predetermined positional relationship, a reference site of an object where an optical fiber plug is not disposed can be measured.

Also, when a reference site of an object is measured, a signal processing unit displays a predetermined display prompting an operator to measure the reference site of the object on a display device after attaching a pseudo plug to an engaging member, and the signal processing unit can be configured so that position data of the reference site of the object measured by a position measurement unit is loaded from the position measurement unit.

Also, when measuring the tip position of an optical fiber, a signal processing unit is configured so that it allows a display device to display a predetermined display to prompt an operator to measure the tip position of the optical fiber after removing a pseudo plug from an engaging member and loads the tip position data of the optical fiber, measured by a position measurement unit, from the position measurement unit. Then, the signal processing unit adds information of the loaded reference position and the tip position of the optical fiber to a living body optical measurement image. Hence, the signal processing unit can create an image where a living body optical measurement image and a morphological image of an object are superimposed using the position information.

Also, in another mode of the present invention, a living body optical measurement method, which measures light passed through an object after irradiating light to the object, is provided. In this method, the tips of plural optical fibers respectively attached to an optical fiber plug are disposed so that the tips come into contact with an object using a holder holding plural optical fiber plugs. Next, a mobile position sensor, to which an engaging member that can be engaged with an optical fiber plug in a predetermined positional relationship is attached, is engaged with plural optical fiber plugs in series using an engaging member, the tip positions of the plural optical fibers are calculated by a position of the mobile position sensor detected at that time and a predetermined positional relationship.

In this method, a pseudo plug is attached to an engaging member in a predetermined positional relationship, the tip of the pseudo plug comes into contact with a reference site of an object on which an optical fiber plug is not disposed, and calculating a reference position (reference position detection process) is also possible by a position of the mobile position sensor detected at that time and a predetermined positional relationship.

Before the reference position detection process, a display prompting an operator to attach a pseudo plug to an engaging member can also be displayed on a display device.

An image where a living body optical measurement image and a morphological image of an object are super imposed can also be created using information of a tip position of an optical fiber by irradiating light from the optical fiber to the object and creating a living body optical measurement image with measured data after taking in light passed through the object from the optical fiber.

Additionally, in another mode of the present invention, an engaging member to be attached to a mobile position sensor of a living body optical measurement apparatus is provided. The engaging member includes an optical fiber plug attached to an optical fiber of the living body optical measurement apparatus and has a shape engaging detachably in a predetermined positional relationship. By using this engaging member, even in the previous living body optical measurement apparatus, a tip position of an optical fiber in a state where it comes into contact with an object can be measured.

Hereinafter, embodiments of the present invention will be described specifically.

First Embodiment (Apparatus Configuration)

Figure 2:
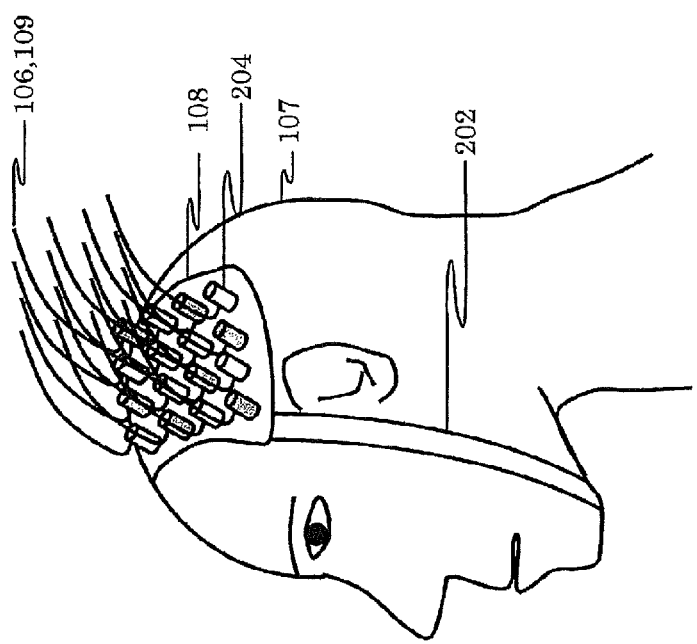
FIG. 2 is a side surface diagram of the object 107 to which the holder 108 is attached.

First, the overall configuration of the apparatus will be described using FIG. 1 etc. FIG. 1 is a block diagram showing the overall configuration of a living body optical measurement apparatus. FIG. 2 is a perspective diagram showing a state where the optical fibers 106 and 109 are attached to the object 107.

A living body optical measurement apparatus is an apparatus that irradiates near-infrared light to the inside of the object 107, detects light reflected from the surface vicinity of a living body or passed through a living body (hereinafter, simply referred to as passing light), and generates electric signals corresponding to a light intensity. As shown in FIG. 1, the living body optical measurement apparatus is comprised of the light irradiation unit 101 irradiating near-infrared light, the light measuring unit 102 measuring passing light to convert into an electric signal, the control unit 103 controlling drives of the light irradiation unit 101 and the light measuring unit 102, the signal processing unit 113, the display device 114, the input/output unit 116, and the storage unit 115.

The light irradiation unit 101 is comprised of the semiconductor laser 104 outputting light of a predetermined wavelength, the optical module 105, and the optical fiber 106. The optical module 105 includes a modulator to modulate light generated by the semiconductor laser 104 in plural frequencies different for each irradiation position. The optical fiber 106 propagates output light from the respective optical modules 105, conducts it to a predetermined measurement region of the object 107 such as plural areas of the head, and irradiates the light to the object 107 from the tip. One or plural wavelengths of the semiconductor laser 104 are selected before use from among the light of the wavelength range of 600 nm to 1,400 nm when the oxygen saturation degree and blood volume are measured from the saturation degrees of oxygenated hemoglobin and deoxygenated hemoglobin in blood depending on the spectral characteristics of a target substance in a living body. Specifically, for example, light of two kinds of wavelengths such as 780 nm and 830 nm is irradiated corresponding to two kinds of measurement targets of oxygenated hemoglobin and deoxygenated hemoglobin. Light of these two wavelengths are synthesized and irradiated to the object 107 from the tip (irradiation position) of the one optical fiber 106.

As shown in FIG. 2, the sheet-like holder 108, to hold an optical fiber, is fixed at the measurement site of the object 107 using the belt (jaw band) 202 etc. A plurality of holes are provided to the holder 108, and rings are fixed on the hole edges. The optical fiber plug 204 is attached to the tip of the optical fiber 106, and the outer periphery of the optical fiber plug 204 is detachably fixed to the holder 108 by being engaged with the ring of the hole edge. Hence, the tip of the optical fiber 106 comes into contact with the surface of a measurement site (for example, the scalp) of the object 107. The structure of the optical fiber plug 204 will be described in detail later.

The light measuring unit 102 includes the optical fiber 109, the photoelectric conversion element 110, the lock-in amplifier module 111, and the A/D converter 112. The optical fiber 109 is disposed so that the tip comes into contact with a predetermined position of a measurement site, absorbs light passed through a predetermined measurement region and output from the surface of an object from among lights irradiated from the light irradiation unit 101 from an end surface of the tip, and propagates the light to the photoelectric conversion element 110. A photoelectric conversion element is a photodiode etc. that convert light propagated by the optical fiber 109 into an electrical quantity corresponding to the respective light amounts. The lock-in amplifier module 111 selectively detects a modulated signal corresponding to a predetermined light irradiation position from among electric signals from the photoelectric conversion element 110. The A/D converter 112 converts an output signal of the lock-in amplifier module 111 into a digital signal. Hence, hemoglobin amount variation signals of a twofold (two-wavelength) number of channels can be obtained compared to the number of points (measurement points) between a light irradiation position (tip position of the optical fiber 106) and a detection position (tip position of the optical fiber 109).

Also, the signal processing unit 113 processes a hemoglobin amount variation signal and generates a graph showing an oxygenated hemoglobin concentration change, deoxygenated hemoglobin concentration change, all the hemoglobin concentration changes, etc. for each channel and an image where the graph is plotted on a two-dimensional image of an object (living body optical measurement image). The display device 114 displays a graph, an image, etc. generated by the signal processing unit 113. The storage unit 115 stores data required for processes by the signal processing unit 113, process results, and generated images.

The input/output unit 116 accepts input of various commands required for apparatus operations from an operator. The control unit 103 controls overall operations of the apparatus and performs living body optical measurement.

In addition to this, a living body optical measurement apparatus includes the three-dimensional position measuring unit 117 in order to measure three-dimensional coordinates of a light irradiation position (the tip of the optical fiber 106) and a detected position (the tip of the optical fiber 109). As the three-dimensional position measuring unit 117, if a three-dimensional position of a mobile position sensor can be detected, units with a variety of measurement methods can be used. Here, the three-dimensional position measuring unit 117 includes the mobile position sensor 118 and the magnetic field generating module 119 and measures a three-dimensional position of the mobile position sensor 118 in the magnetic field generating region 120 generated by the magnetic field generating module 119.

(Structure of the Optical Fiber Plug 204)

Figure 3:
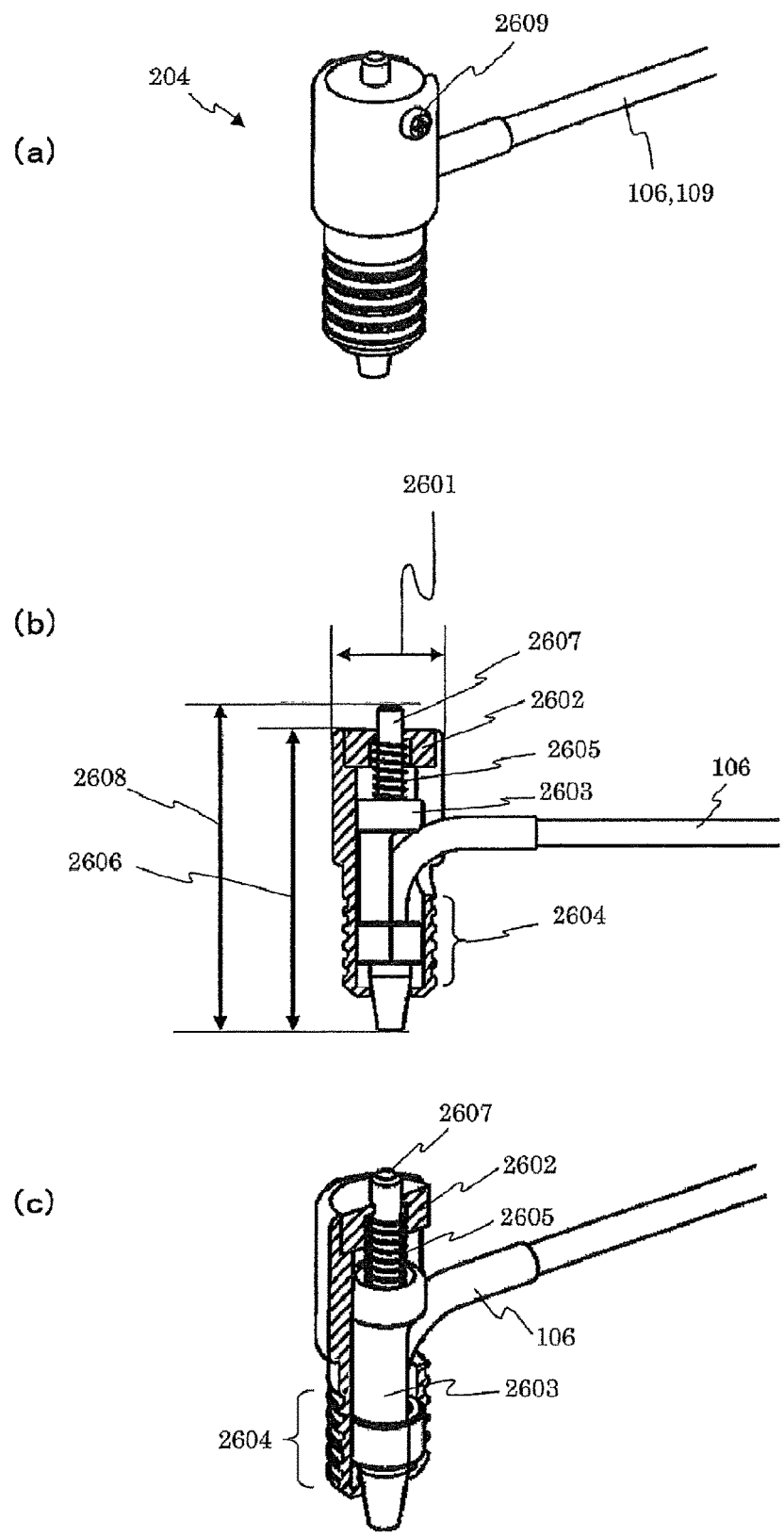
FIGS. 3(a), 3(b), and 3(c) are a perspective diagram, a cross-sectional diagram, and a cross-sectional perspective diagram of the optical fiber plug 204 respectively.

As described above, the optical fiber plugs 204 are attached to the tips of the optical fibers 106 and 109, and the outer periphery of the optical fiber plug 204 is detachably fixed to the holder 108 by being engaged with the ring of the hole edge of the holder 108. Hereinafter, the structure of the optical fiber plug 204 will be described in detail using FIG. 3. FIGS. 3(a), 3(b), and 3(c) are a perspective diagram, a cross-sectional diagram, and a cross-sectional perspective diagram of the optical fiber plug 204 respectively. Because the structure of the optical fiber plug 204 of the optical fiber 106 is the same as that of the optical fiber plug 204 of the optical fiber 109, hereinafter, the optical fiber plug 204 of the optical fiber 106 will be described as an example.

As shown in FIGS. 3(a), 3(b), and 3(c), the optical fiber plug 204 is comprised of the tubular portion 2603 fixed on the outer periphery in the vicinity of the tip of the optical fiber 106, the bar-shaped portion 2607 with a predetermined length fixed on the upper end surface of the tubular portion 2603, the holding portion 2602 disposed on the outer periphery of the tubular portion 2603 and holding the tubular portion 2603 movably in the axial direction, and the spring 2605. The tubular portion 2603 and the bar-shaped portion 2607 comprise a fixing unit fixed to the optical fiber 106. The holding portion 2602 has a shape where a space is created inside the cylinder, the tip of the optical fiber 106 protrudes from the opening provided on the lower end surface, and the bar-shaped portion 2607 protrudes from the opening provided on the upper end surface. The optical fiber 106 is bent inside the optical fiber plug 204, is pulled out of the opening provided on the side surface of the tubular portion 2603, and is further pulled out to the outside through the opening provided on the side surface of the tubular holding portion 2602. Hence, the optical fiber 106 is pulled out in a direction bent almost 90 degrees to the axial direction of the tip of the optical fiber 106.

The tubular portion 2603 and the bar-shaped portion 2607 can move in the axial direction with the optical fiber 106 inside the holding portion 2602. Therefore, an amount of protrusion from the holding portion 2602 of the optical fiber 106 is variable. The spring 2605 is disposed on the outside of the bar-shaped portion 2607 and is biased in a direction where the tubular portion 2603 is pressed down to the upper end surface of the holding portion 2602. Because the spring 2605 is biased, the tip surface of the optical fiber 106 can come into contact with the surface (scalp) of an object at an appropriate pressing force.

In the lower section of the holding portion 2602, the male screw-shaped protrusions 2604 are provided at a predetermined pitch on the outer periphery. The protrusions 2604 are engaged with a ring fixed around the hole of the holder 108 and detachably fix the optical fiber plug 204 on the holder 108.

Because the bar-shaped portion 2607 is a member fixed to the optical fiber 106 and having a certain length, the distance 2608 from the upper end of the bar-shaped portion 2607 to the tip of the optical fiber 106 is constant. Therefore, the tip of the mobile position sensor 118 comes into contact with the upper end of the bar-shaped portion 2607 in order to detect the three-dimensional position, which can calculate a position distant by the distance 2608 in the axial direction, and the calculated result can be used to calculate a tip position of the optical fiber 106. Also, because the holding portion 2602 is movable to the optical fiber 106, the distance 2606 from the upper end surface of the holding portion 2602 to the tip of the optical fiber 106 fluctuates depending on a position fixed to the holder 108 of the holding portion 2602.

Also, an operator can check how much the spring 2605 is compressed by visually checking the length of the bar-shaped portion 2607 protruding from the upper end from the holding portion 2602. As shown in FIG. 4(a), when the length of the bar-shaped portion 2607 protruding upward is long, the spring 2605 is greatly compressed, and the pressing force of the optical fiber 106 by the spring 2605 is large. Therefore, the optical fiber 106 is pressed on the surface of the object 107 at a relatively strong pressing force, and the object 107 may feel the pain. Conversely, as shown in FIG. 4(b), when the length of the protruding bar-shaped portion 2607 is short, the pressing force of the optical fiber 106 by the spring 2605 is small, and the optical fiber 106 rises up from the surface of the object 107 and may not come into contact with the surface. An operator adjusts a position where the holding portion 2602 is being held by the holder 108, performs adjustment so that the bar-shaped portion 2607 protrudes from the holding portion 2602 by an appropriate length, and can appropriately set a pressing force to the object 107 of the optical fiber 106.

Figure 5:
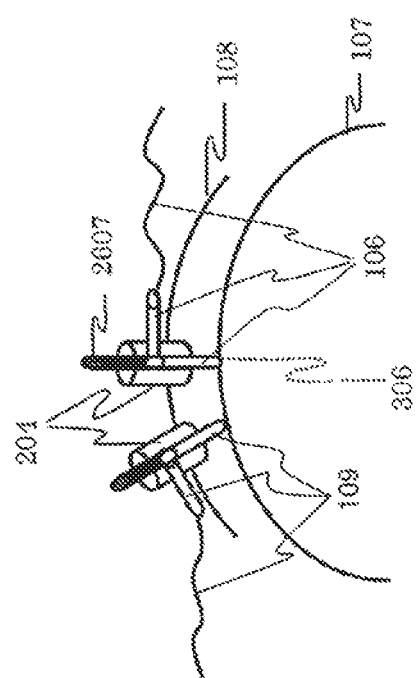
FIG. 5 is an explanatory diagram showing a state where the optical fiber plug 204 is fixed in the holder 108 from the cross-sectional direction of the holder 108.

The optical fiber plugs 204 with such a structure are inserted in holes arranged and provided on the holder 108 as shown in FIG. 2 in order to engage the male screw-shaped protrusions 2604 with the rings around the holes, which can press the tip surface of the optical fiber 106 onto the surface of the object 107 at a predetermined pressing force. At this time, head hair is combed with a slim stick etc. so that the head hair is not caught between the tip of the optical fiber 106 and the surface of the object 107. FIG. 5 is a view showing a state where the optical fiber plug 204 is fixed to the holder 108 so that the tips 306 of the optical 106 and 109 are pressed onto the surface of the object 107 when viewed from the cross-sectional direction of the holder 108. Thus, the optical fiber plugs 204 of all the optical fibers 106 of the light irradiation unit 101 and the optical fiber plugs 204 of all the optical fibers 109 of the light measuring unit 102 are fixed to the holder 108 in a predetermined arrangement. Normally, the total number of the optical fibers 106 and 109 is 30 to 80.

Also, on the upper outer periphery of the holding portion 2602, the screw 2609 to connect a tubular side surface member of the holding portion 2602 and a member of the upper end surface is provided. Because the screw 2609 protrudes from a side surface of the holding portion 2602, the engaging member 502 to be described later has a concave portion in a position corresponding to the screw 2609.

(The Mobile Position Detection Sensor 118 and the Engaging Member 502)

Figure 6:
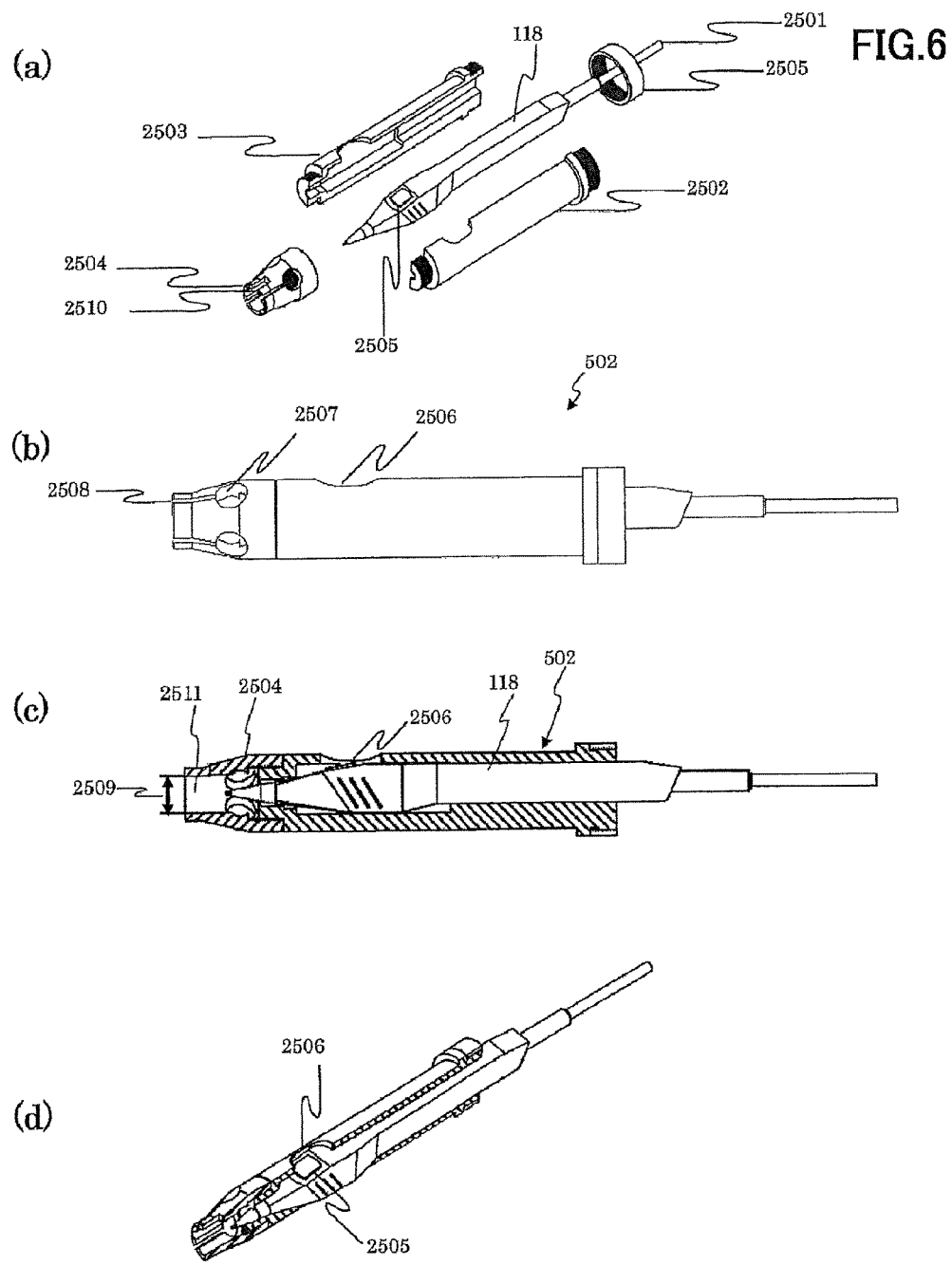
FIG. 6(a) is a perspective diagram of the mobile position sensor 118 and the parts of the engaging member 502.
FIGS. 6(b), 6(c), and 6(d) are a side surface diagram, a cross-sectional diagram, and a cross-sectional perspective diagram of a state where the engaging member 502 is fixed to the mobile position sensor.

FIG. 6(a) is a perspective diagram of the mobile position sensor 118 and the parts of the engaging member 502 to be fixed to the sensor. FIGS. 6(b), 6(c), and 6(d) are a side surface diagram, a cross-sectional diagram, and a cross-sectional perspective diagram of a state where the engaging member 502 is fixed to the mobile position sensor.

The mobile position sensor 118 is pen-shaped as shown in FIG. 6(a) and has the button 2505 on a side surface. When an operator presses down the measurement button 2505 on a side surface, the three-dimensional position measuring unit 117 measures a three-dimensional position of the tip of the mobile position sensor 118.

The engaging member 502 is attached to a mobile position sensor and has a shape (opening) engaged with the optical fiber plug 204 held by the holder 108 detachably in a predetermined positional relationship.

The engaging member 502 is comprised of the four parts of the left-side body portion 2502, the right-side body portion 2503, the opening portion 2504 engaged with the optical fiber plug 204, and the nut 2505. Because the mobile position sensor 118 is a magnetic sensor, the respective parts are comprised of non-magnetic materials (for example, plastic) that do not generate magnetic noise.

The left-side body portion 2502, the right-side body portion 2503, and the nut 2505 are members to fix the opening portion 2504 engaged with the optical fiber plug 204 to the mobile position sensor 118.

The left-side body portion 2502 and the right-side body portion 2503 have a space to accommodate the mobile position sensor 118 in the inside and have a shape holding the mobile position sensor 118 between them. Threads are provided on the tips and tails of the left-side body portion 2502 and the right-side body portion 2503, the engaging member 502 is integrally fixed to the mobile position sensor by threadably mounting the opening portion 2504 on the tip and the nut 2505 on the tail.

In the mobile position sensor 118 position of the left-side and right-side body portions 2502 and 2503, the button hole 2506 is provided so that an operator can press down the measurement button 2505.

The opening portion 2504 has the opening 2511 with a shape engaged with an outer periphery of the holding portion 2602 of the optical fiber plug 204 on the edge. That is, the diameter of the opening 2511 has a length where a predetermined clearance is added to the outer shape of the holding portion 2602. The opening 2511 has the notch 2510 with a size in which the optical fibers 106 and 109 pulled out of a side surface of the holding portion 2602 can be inserted, and inserting the optical fibers 106 and 109 in the notch 2508 does not interfere the engagement. Also, on the internal surface of the opening 2511, a concave portion with a shape corresponding to the screw 2609 that protrudes from a side surface of the holding portion 2602 is formed.

Figure 7:
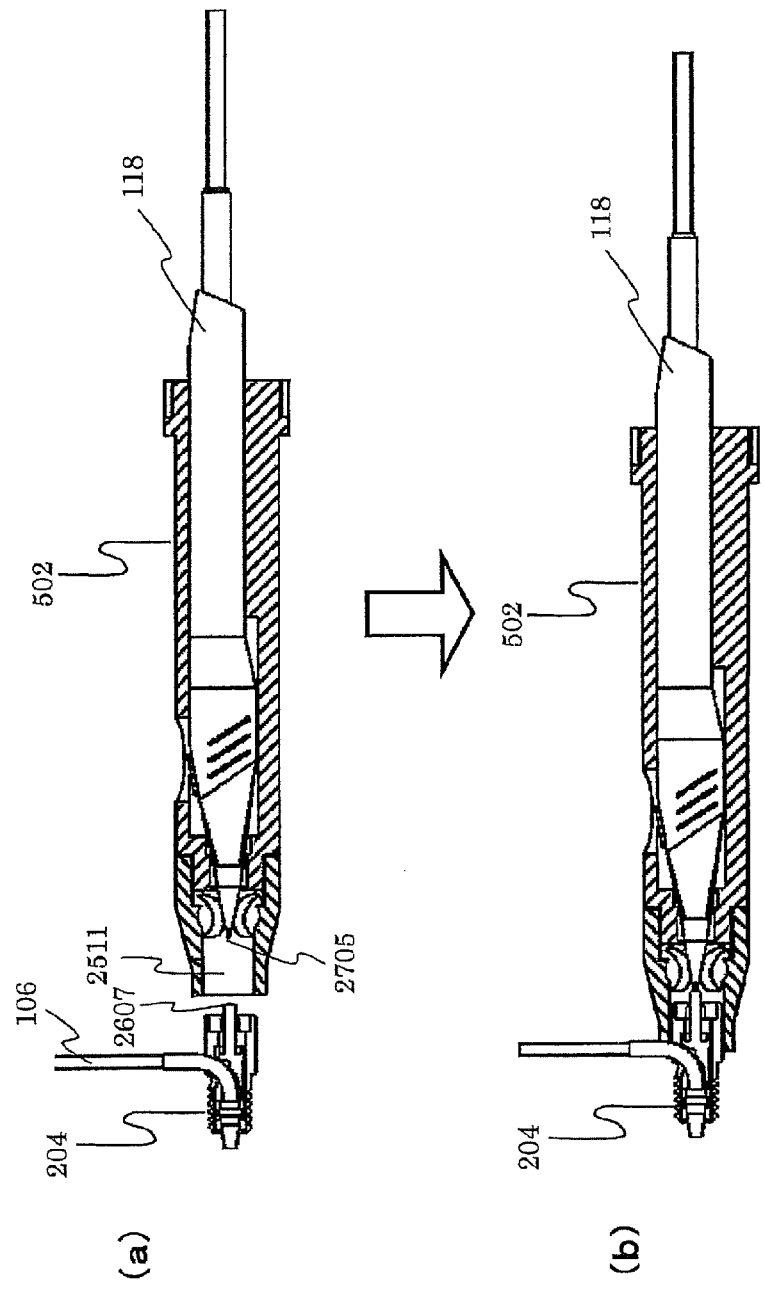
FIG. 7(a) is a cross-sectional diagram of the engaging member 502 before the optical fiber plug 204 is inserted.
FIG. 7(b) is a cross-sectional diagram of the engaging member 502 after the optical fiber plug 204 is inserted.

The axial direction of the opening portion 2504 is configured so that it corresponds to the axial direction of the mobile position sensor 118. Hence, as shown in FIGS. 7(a) and 7(b), engaging (inserting) the optical fiber plug 204 with (in) the opening 2511 of the opening portion 2504 can correspond the axial direction of the tip of the optical fiber 106 to that of the mobile position sensor 118.

Also, the window 2507 is opened on the side surface of the opening portion 2504 of the engaging member 502 so that an operator can check the tip of the mobile position sensor 118. As shown in FIGS. 7(a) and 7(b), by visually checking the tip 2705 of the mobile position sensor 118 from the window 2507 while the optical fiber plug 204 is being engaged with (inserted in) the opening 2511 of the opening portion 2504, the engaging member 502 and the mobile position sensor 118 can be moved toward the optical fiber plug 204 up to the position where the tip of the bar-shaped member 2607 of the optical fiber plug 204 comes into contact with the tip 2705 of the mobile position sensor 118.

Figure 8:
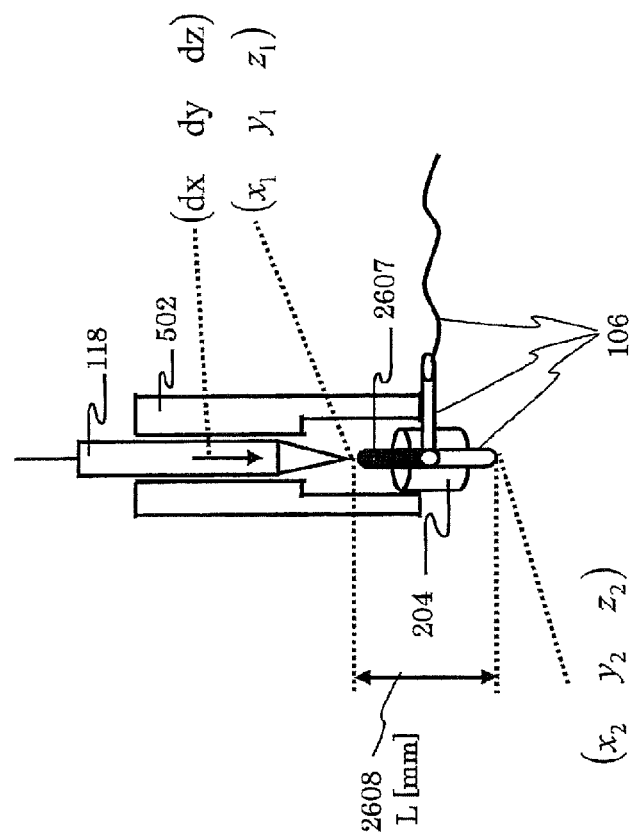
FIG. 8 is an explanatory diagram showing a tip coordinate and an axial-direction vector of the mobile position sensor 118 and a tip coordinate of an optical fiber in a state where the optical fiber plug 204 is inserted in the engaging member 502.

When the tip of the mobile position sensor 118 comes into contact with the bar-shaped member 2607, an operator presses down the measurement button 2505. As shown in FIG. 8, the three-dimensional position measuring unit 117 measures a position coordinate (x1, y1, z1) of the tip of the mobile position sensor 118 and an axial direction vector (dx, dy, dz) of the tip of the mobile position sensor 118. However, the unit of (x1, y1, z1) is mm, and that of (dx, dy, dz) is a non-dimensional quantity and represented as √(dx2+dy2+dz2)=1. The signal processing unit 113 reads and executes a built-in program and calculates a coordinate (x2, y2, z2) of a position remote by a predetermined distance (L) 2608 in the axial direction of the mobile position sensor 118 from a position measured by the three-dimensional position measuring unit 117 using the following formula (1).

$$(x2,y2,z2)=(x1,y1,z1)+L\times(dx,dy,dz) \quad (1)$$

Hence, the tip position (x2 y2 z2) of the optical fiber 106 can be calculated.

Also, on a side surface of the opening portion 2511 of the engaging member 502, the several small slots 2508 are provided along the axial direction. Hence, even if sizes of the outer diameter 2601 of the holding portion 2602 of the optical fiber plug 204 vary, the plug can be inserted in (engaged with) the opening 2511 smoothly.

The living body optical measurement needs to measure positions of the reference points (for example, a nasion (nasal root), a right ear upper-end portion, a left ear upper-end portion, etc.) on the object 107 to which the optical fibers 106 and 109 are not attached. Because the optical fibers 106 and 109 are not attached to the reference points, the optical fiber plug 204 does not exist. Therefore, although it is considered to detach the engaging member 502 from the mobile position sensor 118 in order to measure the positions of the reference points on the object 107, operations to detach and re-attach the engaging member 502 are very complicated. Also, being different from a case where the engaging member 502 is attached, if the engaging member 502 is detached, calculation of the signal processing unit 113 does not need to be performed, and a position calculated by the three-dimensional position measuring unit 117 must be used as is. Therefore, the calculation method must be changed depending on whether the reference points are measured or whether the tips of the optical fibers 106 and 109 are measured, and this is very complicated.

Figure 9:
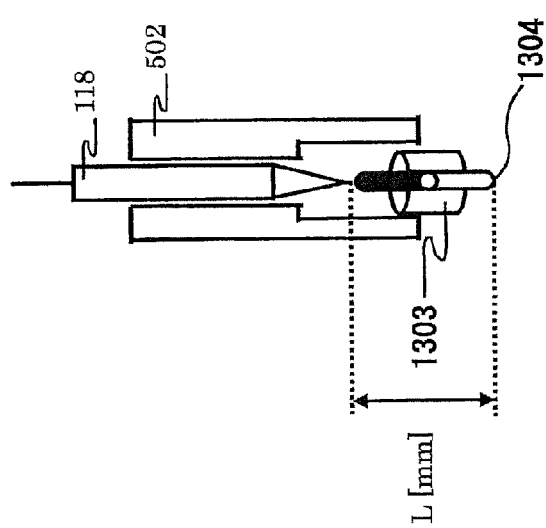
FIG. 9 is an explanatory diagram showing a state where a pseudo plug is attached to the engaging member 502.

In the present invention, in a case where the reference points are measured, the pseudo plug 1303 with the same shape and size as the optical fiber plug 204 is inserted in the opening 2511 of the engaging member 502 as shown in FIG. 9. Specifically, the distance L from the tip of the pseudo plug 1303 to the tail is designed so as to be the same as the distance 2608 from the tip of the optical fiber 106 in FIG. 3(b) to the upper end of the bar-shaped member. Hence, an operator can detect positions of the reference points by contacting the tip 1304 of the pseudo plug 1303 with a reference point and pressing down the measurement button 2505. Therefore, without complicated operations such as detaching and re-attaching the engaging member 502 and a need to change a calculation method of the signal processing unit 113, positions of the reference points on an object can be easily measured.

(Living Body Optical Measurement Method)

Next, a method to create an image where a morphological image of an object such as an MRI image measured separately is superimposed on a living body optical measurement image will be described using FIG. 10 etc. Since the details of the process to create a superimposed image of a morphological image such as an MRI image and a living body optical measurement result are described in PTL 1 etc. and a publicly known technique, the overview will be described here, and the optical fiber and the method to measure positions of the reference points of the present invention in the process will be described in detail.

First, an operator fixes the optical fiber plugs 204 of all the optical fibers 106 and 109 to the holes of the holder 108 in order and disposes them so that the tips of the optical fibers 106 and 109 come into contact with the surface of the object 107 at a predetermined pressure. After a living body optical measurement is performed in this state, a living body optical measurement image may be created, and a living body optical measurement may also be performed after Step 1205. In the living body optical measurement, under the control by the control unit 103, light is irradiated to the object 107 from the optical fiber 106 of the light irradiation unit 101, the optical fiber 109 absorbs the light passed through the object 107 to detect the light, and then the signal processing unit 113 creates a living body optical measurement image.

Figure 10:
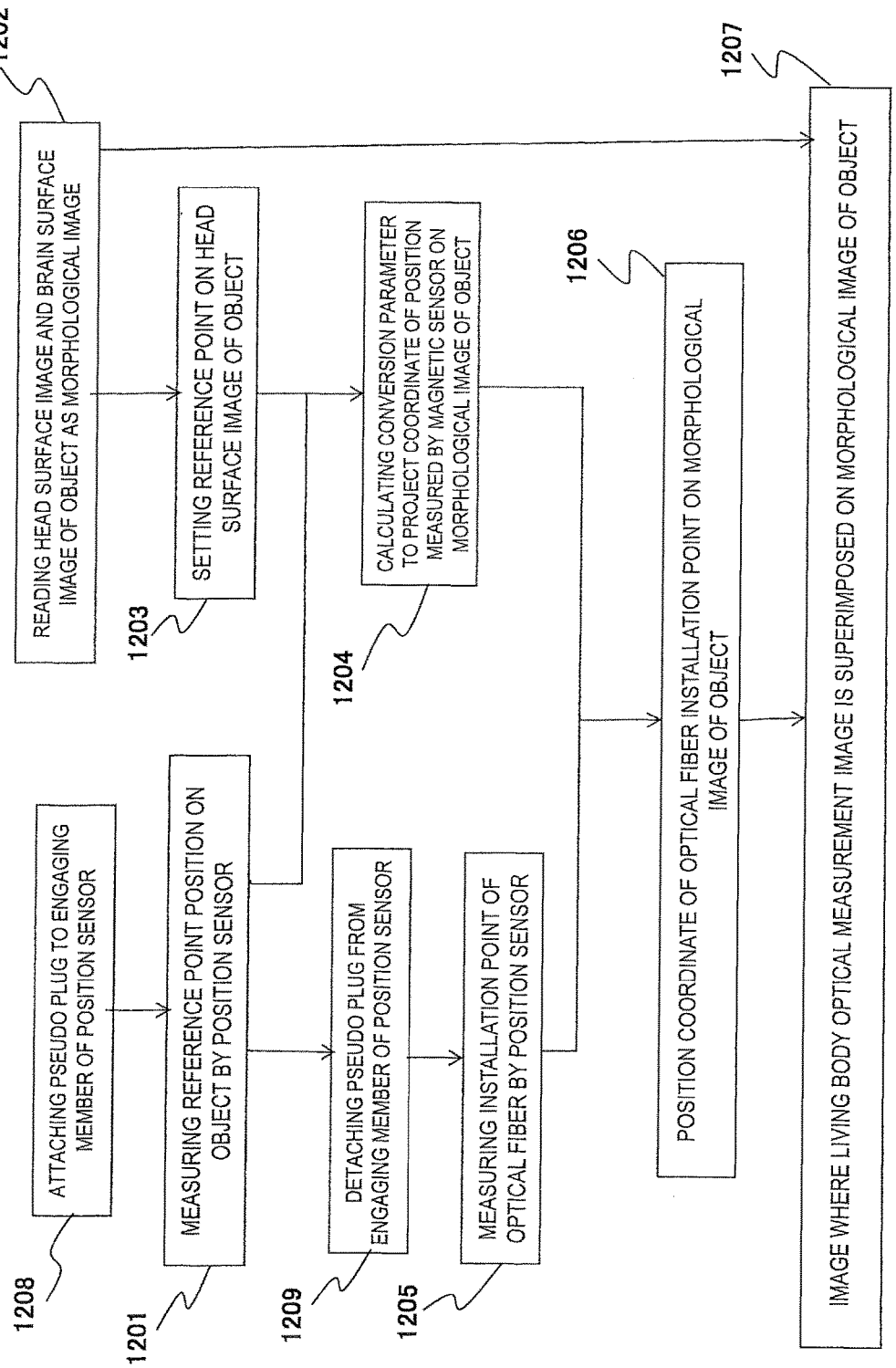
FIG. 10 is a flow chart showing a process of a living body optical measurement method of the first embodiment.

When an operator operates the input/output unit 116 to start up the main screen 2801 for the optical fiber position measurement in FIG. 11(a), the signal processing unit 113 displays a message prompting to attach the pseudo plug (referred to also as "dummy plug") 1303 to the engaging member (referred to also as "magnetic sensor cover") 502 before the mobile position sensor 118 measures positions of the reference points on the object 107 on the message window 2802 (Step 1208 in FIG. 10).

Pressing the "Cancel" button on the message window 2802 closes the main screen 2801 for the optical fiber position measurement to stop the optical fiber position measurement.

According to a message on the message window 2802, an operator attaches the pseudo plug 1303 to the engaging member 502 and presses the "OK" button, which displays the screen shown in FIG. 11(b). In the screen of FIG. 11(b), the display region 2803 displaying a living body optical measurement result of the reference points (for example, a nasion (nasal root), a right ear upper-end portion, a left ear upper-end portion, etc.) on the object 107 measured by the mobile position sensor 118 is displayed. When an operator contacts the tip of the pseudo plug 1303 with the reference points on an object and presses the measurement button 2505, the three-dimensional position measuring unit 117 searches for a position of the mobile position sensor 118 at that time, and then signal processing unit 113 calculates positions of the reference points on an object using the formula (1) described previously (Step 1201). The calculated positions of the reference points are displayed in the display region 2803 as shown in FIG. 12(a) as well as are stored in a predetermined region inside the storage unit 115. This is repeated until all the reference points are measured.

When the position data for all the reference points is stored, as shown in FIG. 12(b), the signal processing unit 113 displays a message prompting to detach the pseudo plug 1303 from the engaging member 502 of the mobile position sensor 118 on the message window 2804. Pressing the "Cancel" button on the message window 2804 displays the screen shown in FIG. 11(b), which can measure positions of the reference points on the object 107 again.

Figure 13:
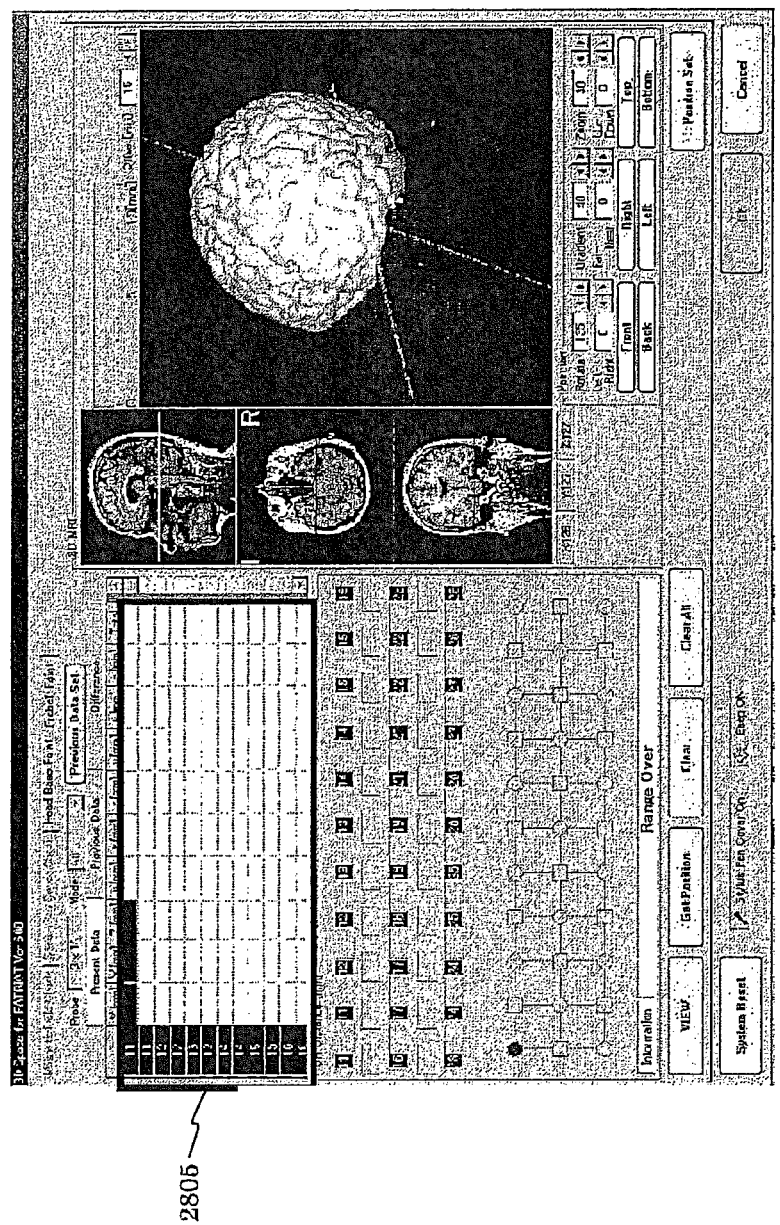
FIG. 13 is an explanatory diagram showing a screen example that the signal processing unit 113 displays on the display device 114 in a living body optical measurement method.
Figure 14:
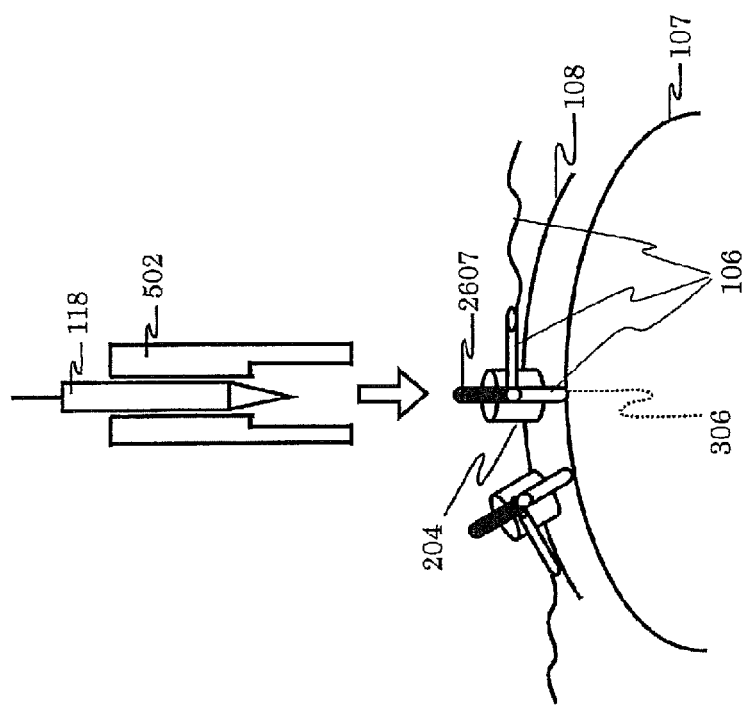
FIG. 14 is an explanatory diagram showing that the engaging member 502 approaches along the axial direction of the tip of the optical fibers 106 in a state where the optical fiber plug 204 has been fixed in the holder 108.

When an operator presses the "OK" button on the message window 2804 after detaching the pseudo plug 1303 from the engaging member 502 of the mobile position sensor 118 according to the message, the screen shown in FIG. 13 appears, the position measurement of the reference points on the object 107 (Step 1201) is completed, which can measure the optical fibers 106 and 109 by the mobile position sensor 118 (Step 1205). Specifically, as shown in FIGS. 7(a) and 14, the engaging member 502 approaches along the axial direction of the tip of the optical fiber 106 without shifting a position of the optical fiber plug 204 while it is being fixed on the holder 108.

Figure 15:
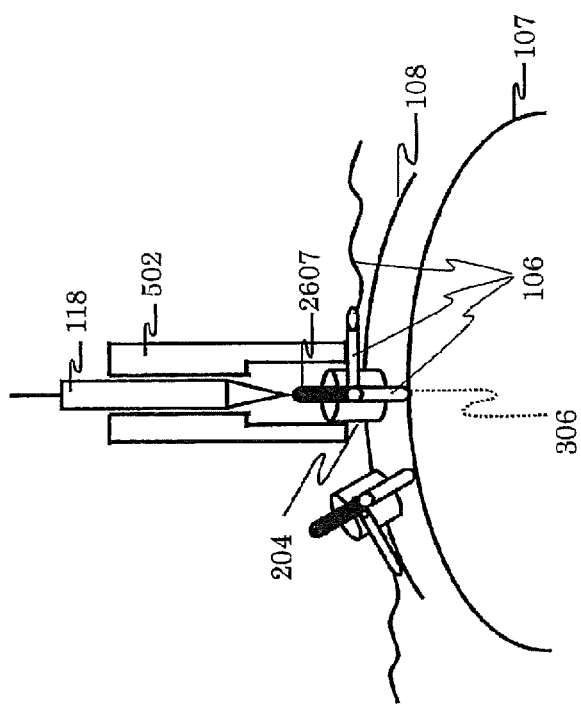
FIG. 15 is an explanatory diagram showing a state the optical fiber plug 204 is inserted (engaged) in the opening 2511 of the engaging member 502.

Then, as shown in FIGS. 7(b) and 15, the optical fiber plug 204 is inserted in (engaged with) the opening 2511 of the engaging member 502, and then the tip of the mobile position sensor 118 comes into contact with the upper end of the bar-shaped member 2607. The contact state can be checked visually from the window 2507 of the opening portion 2504 by an operator. When an operator presses down the measurement switch 2505 in this state, the three-dimensional position measuring unit 117 searches for a position of the mobile position sensor 118 at that time, and then the signal processing unit 113 calculates a position of the tip 306 of the optical fiber 106 using the formula (1) described previously (Step 1205). The calculated position of the tip 306 of the optical fiber 106 is displayed in the display region 2805 of FIG. 13 and is stored in a predetermined region inside the storage unit 115. This is repeated until all the optical fibers 106 and 109 are measured.

On the other hand, the signal processing unit 113 reads a morphological image of an object measured separately (a head surface image and a brain surface image of an MRI image, CT image, etc. of an object) (Step 1202). The signal processing unit 113 searches for positions of the reference points (for example, a nasion (nasal root), a right ear upper-end portion, a left ear upper-end portion, etc.) by performing image processing etc. for the loaded morphological image (Step 1203).

The signal processing unit 113 calculates a transformation parameter to project a position coordinate of the reference points calculated in Step 1201 onto the reference points, calculated in Step 1203, of the morphological image of an object (Step 1204).

The signal processing unit 113 projects the tip positions of the optical fibers 106 and 109 searched in Step 1205 onto a morphological image using a calculated transformation parameter in order to calculate the position coordinate (Step 1206).

Figure 16:
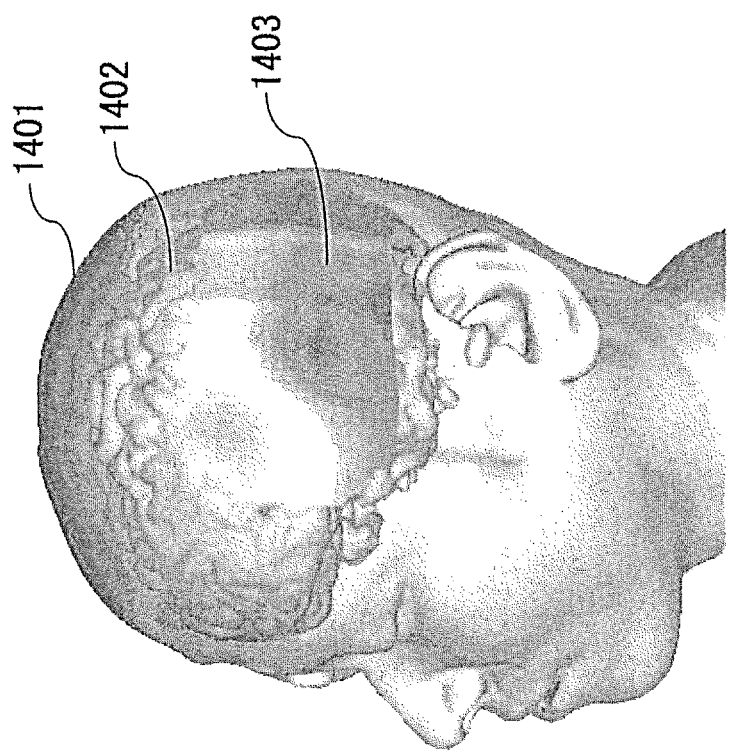
FIG. 16 is an explanatory diagram showing a superimposed image of the morphological image 1402 of an object is and the living body optical measurement image 1403.

Using a position coordinate of the tip of the optical fibers 106 and 109 on a morphological image, a living body optical measurement image is projected onto the morphological image, and an image where the living body optical measurement image is superimposed on the morphological image is created (Step 1207). Hence, for example, the image 1401 where the living body optical measurement image 1403 is superimposed on the morphological image 1402 can be created as shown in FIG. 16. The signal processing unit 113 displays the created superimposed image 1401 on the display device 114 and stores it in the storage unit 115.

(Time Required to Measure a Position of the Optical Fiber)

Figure 17:
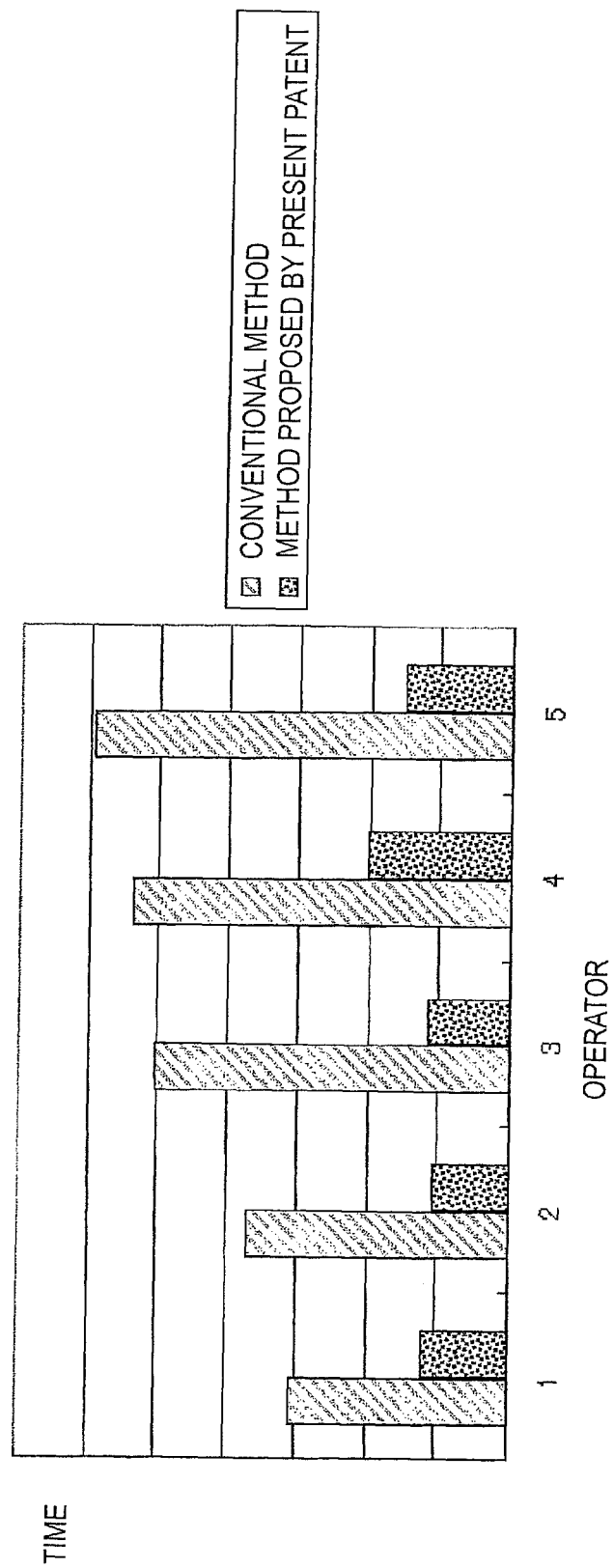
FIG. 17 is a graph showing comparison of time required to measure tip positions of optical fibers between the measurement method of the present invention and that of a comparison example.

Operation time required to measure positions of 32 pieces of the optical fibers 106 and 109 using the position measurement method of the present embodiment described above was measured. The results are shown in FIG. 17. The vertical axis of FIG. 17 represents the operation time required for the operation, and the horizontal axis represents five operators.

Figure 18:
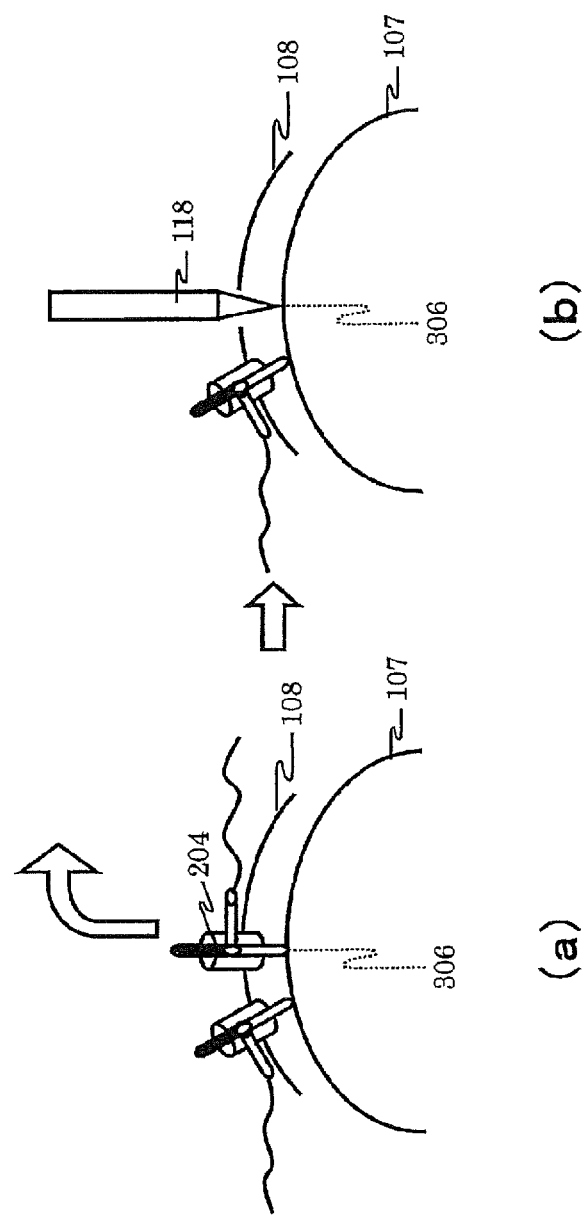
FIGS. 18(a) and 18(b) are explanatory diagrams showing a method to measure tip positions of optical fibers of a comparison example.

As a comparison example, operation time required to similarly measure positions of 32 pieces of the optical fibers using the conventional measurement method is shown. In the position measurement method of the comparison example, as shown in FIGS. 18(*a*) and 18(*b*), the optical fiber plug 204 is detached from the holder 108 once, the mobile position sensor 118 is inserted in positions where an operator presumes that there were the tip positions 306 of the detached optical fibers 106 and 109 to measure the positions, and then the optical fiber plug 204 is attached to the holder 108 again.

As in clear from FIG. 17, compared to the position measurement method of the comparison example, it is clear that the operation time was shortened significantly for all the five operators when the measurement method of the present invention was used. Also, although the operation time required for the position measurement varies depending on the operator's skill, the measurement method of the present invention could complete the position measurement in an approximately 30% operation time for when the method of the comparison example is used.

In the method of the comparison example, attention is needed so that a position of the holder 108 for the object 107 is not shifted when the optical fiber plug 204 is detached from the holder 108. Whether a position of the holder 108 for the object 107 is shifted or not depends on the operator's skill. Also, an operator measures a position presumed as the tip position 306 of the optical fiber 106 at a rough estimate using the mobile position sensor after the optical fiber plug 204 is detached from the holder 108, which results in a problem where errors are superimposed easily. On the contrary to this, the measurement method of the present invention does not need to detach the optical fiber plug 204 from the holder 108 and can measure a tip position of the optical fiber in a highly accurate way by directly measuring the tip position of the optical fiber.

Also, as shown in FIG. 3, although the present embodiment has a structure where the optical fiber plug 204 is separated into the portions 2603 and 2607 fixed by the optical fiber 106 and the holding portion 2602 holding them, and the spring 2605 is disposed between them, the present invention is not limited to this structure. Measuring a position of the plug fixed by the optical fibers 106 and 109 using the mobile position sensor 118 can obtain the similar effect.

Figure 19:
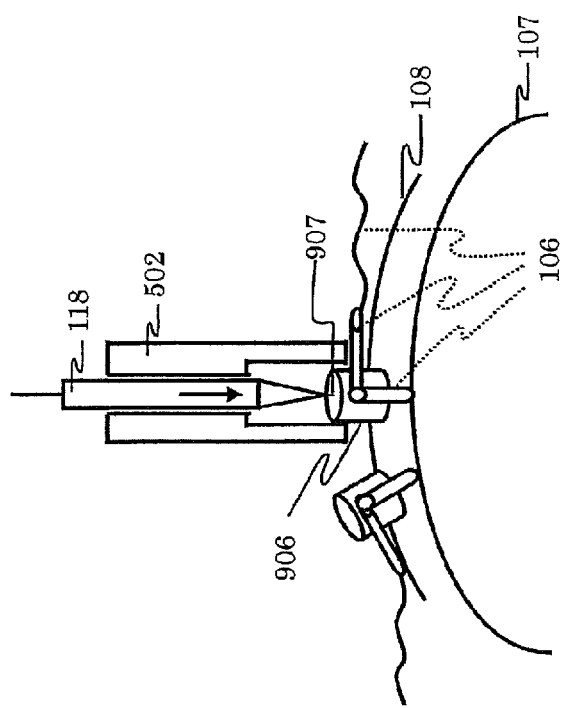
FIG. 19 is an explanatory diagram showing a state where the optical fiber plug 906 comprised of only parts fixed by the optical fibers 106 is inserted in the engaging member 502.

For example, as shown in FIG. 19, in the case of the optical fiber plug 906 that is comprised of only the portion fixed to the optical fiber 106, a position of the upper surface 907 of the optical fiber plug 906 can be measured with the mobile position sensor 118.

Figure 20:
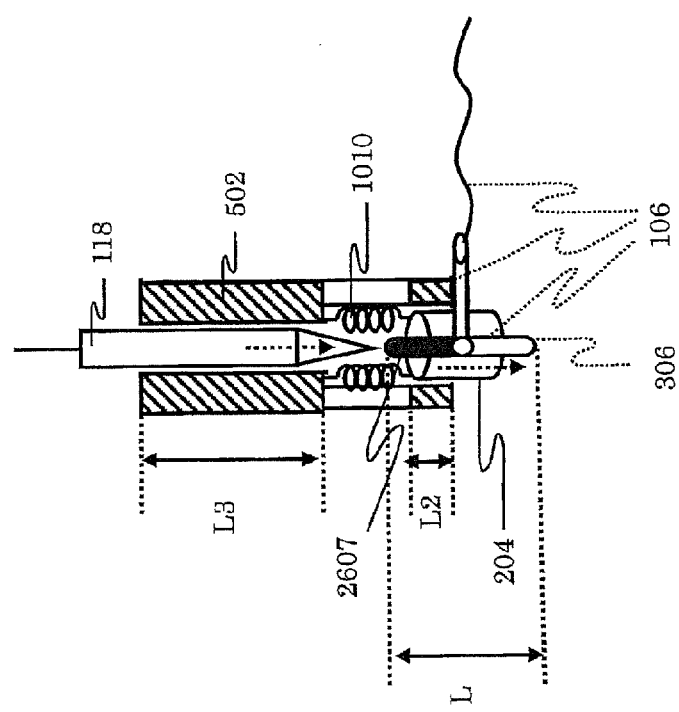
FIG. 20 is an explanatory diagram showing the other configuration example of the engaging example 502.

In the present embodiment, since a three-dimensional position of the tip 306 of the optical fiber 106 is calculated from a position of the contact portion of the mobile position sensor 118 and the bar-shaped member 2607, it is desirable that the distance L from the upper end of the bar-shaped member 2607 to the tip 306 of the optical fiber is shorter in the light of reducing a measurement error. On the other hand, as shown in FIG. 20, in order to match the orientation of the mobile position sensor 118 with that of the optical fiber plug 204, it is desirable that the length L2 of the optical fiber plug 204 to be inserted in the opening of the engaging member 502 is longer, at least 1 cm or longer. Considering the above requirements for L and L2 and the structural limitations of the optical fiber plug 204, L and L2 can be set to approximately 2 to 5 cm and approximately 1 to 3 cm respectively as an example.

In order to match the orientation of the mobile position sensor 118 with that of the optical fiber plug 204, it is desirable that the length L3 of the holding portions (the body portions 2502 and 2503) of the engaging member 502 by an operator is longer. On the other hand, considering the handling of the holding portions (the body portions 2502 and 2503) of the engaging member 502 by an operator, it is desirable that the length of L3 is easy to handle. Considering the above, the length L3 of the engaging member 502, as an example, can be designed that it is approximately 8 to 15 cm.

Also, in order to detach the engaging member 502 smoothly from the optical fiber plug 204 after engaging the engaging member 502 with the optical fiber plug 204, the following configuration can be adopted for the engaging member 502. For example, applying a lubricant on the inside of the opening 2511 of the engaging member 502 in advance enables the engaging member 502 to be connected to and detached from the optical fiber plug 204 smoothly. Also, as shown in FIG. 20, it can be configured that the spring 1010 made of non-magnetic materials such as plastic is disposed inside the opening 2511 of the engaging member 502 in order to create the repulsion force of the spring 1010 between the engaging member 502 and the upper surface of the optical fiber plug 204 so that the engaging member 502 is detached from the optical fiber plug 204 smoothly.

Second Embodiment

Although a living body optical measurement image is superimposed on a morphological image of an object in the first embodiment, the present invention is not limited to this. In the second embodiment, a superimposed image of a pseudo-morphological image of an object and a living body optical measurement result is created.

Figure 21:
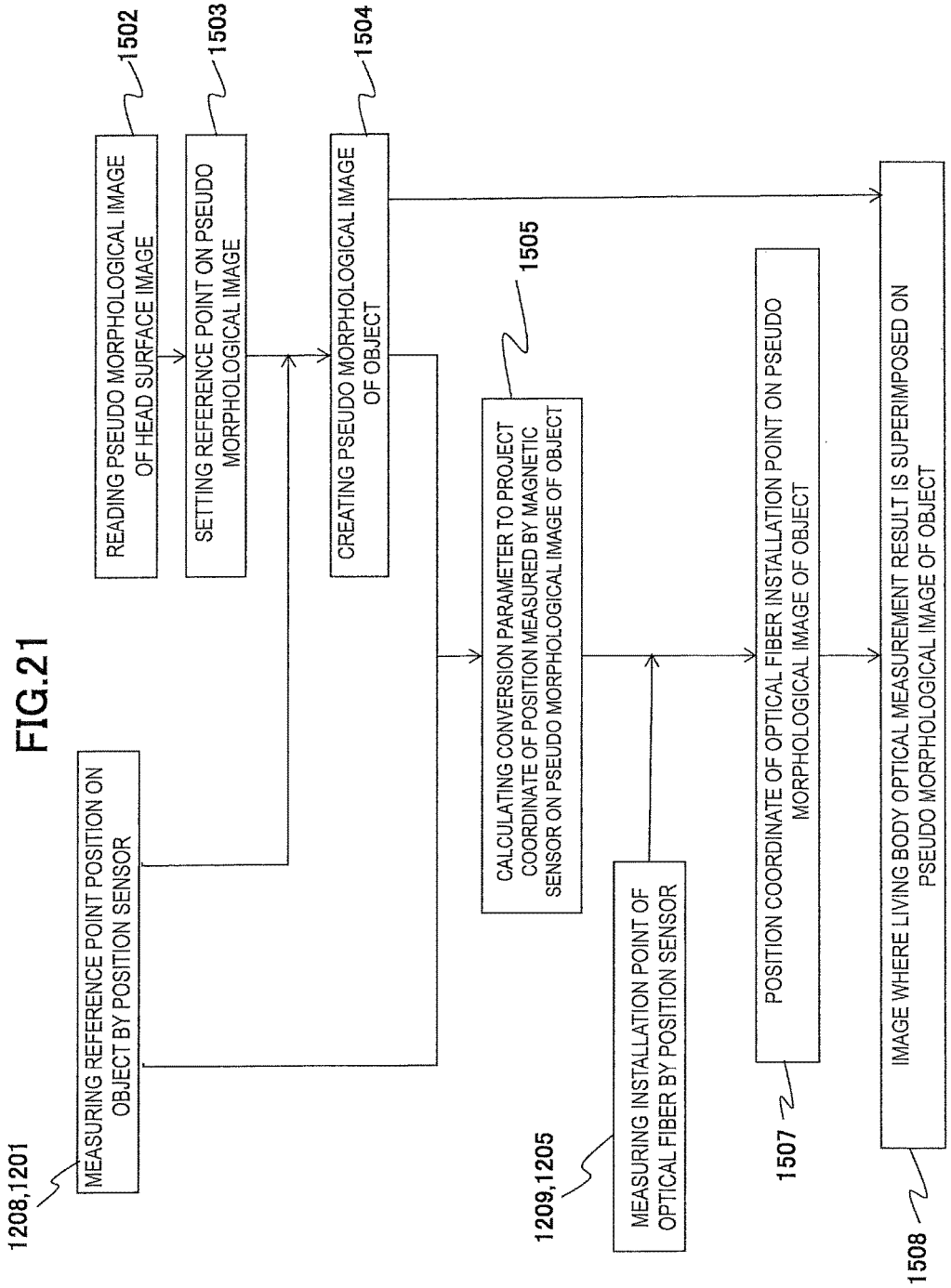
FIG. 21 is a flow chart showing a process of a living body optical measurement method of the second embodiment.

The image creation process for superimposing a pseudo-morphological image of the head surface image of an object and a living body optical measurement result is shown in FIG. 21. Since the image creation process for superimposing a pseudo-morphological image of the head surface image of an object and a living body optical measurement result is the publicly known method described in PTL 1, U.S. Pat. No. 4,266,453, etc. in detail, the overview will be described here, and points to which the present invention is applied in the process will be described hereinafter.

Because an MRI apparatus and a CT apparatus are expensive, it may often be difficult to obtain a morphological image of an object such as an MRI image. In such case, by using a pseudo morphological image of a head surface image of the object 107, a living body optical measurement result can be displayed on the pseudo morphological image of the object in a simple way.

First, similarly to Steps 1208 and 1201 in FIG. 10 of the first embodiment, positions of the reference points on an object are measured by the mobile position sensor 118.

Next, a pseudo morphological image of a head surface image prepared in advance is read (Step 1502). In the present embodiment, a wire frame image is used as a pseudo morphological image. On the read pseudo morphological image, predetermined reference points (a nasion (nasal root), a right ear upper-end portion, a left ear upper-end portion, etc.) are searched for by image processing etc. (Step 1503).

Figure 4:
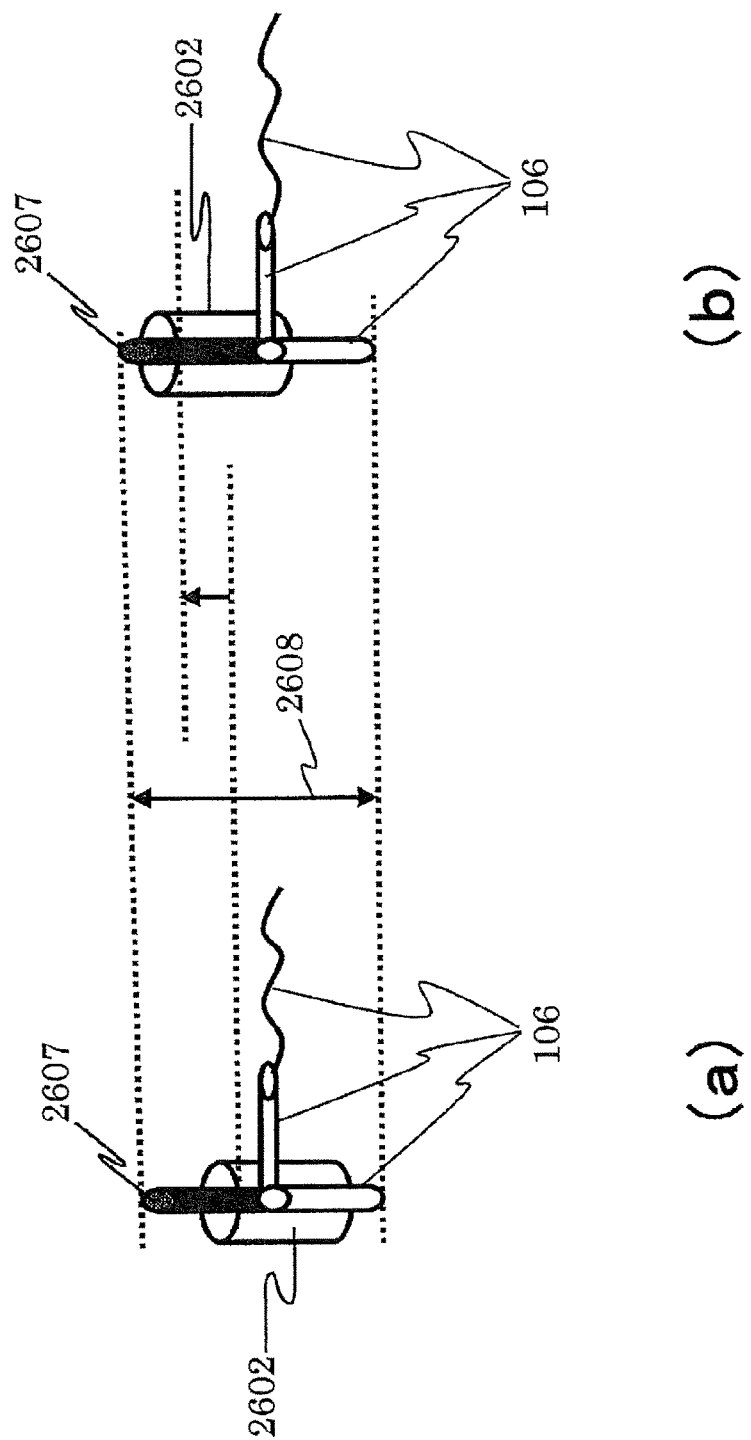
FIGS. 4(a) and 4(b) are explanatory diagrams showing a pressure difference between the optical fibers 106 according to the protruding length of the bar-shaped member of the optical fiber plug 204.

Next, using positions of the reference points of the object 107 measured in Step 1201 and those in the pseudo morphological image that is described above and prepared in advance, dimension correction etc. are performed for the pseudo morphological image to create a pseudo morphological image of reference points corresponding to the positions of the reference points of the object 107 (Step 1504). Thus, the creation method for a pseudo morphological image (wire frame image) is a publicly known technique described in U.S. Pat. No. 4,266,453 (FIG. 4 etc.).

Then, similarly to Step 1204 of the first embodiment, a transformation parameter is calculated where positions of the reference points measured on the object 107 are projected as the reference points on a pseudo morphological image of an object (Step 1505).

Figure 22:
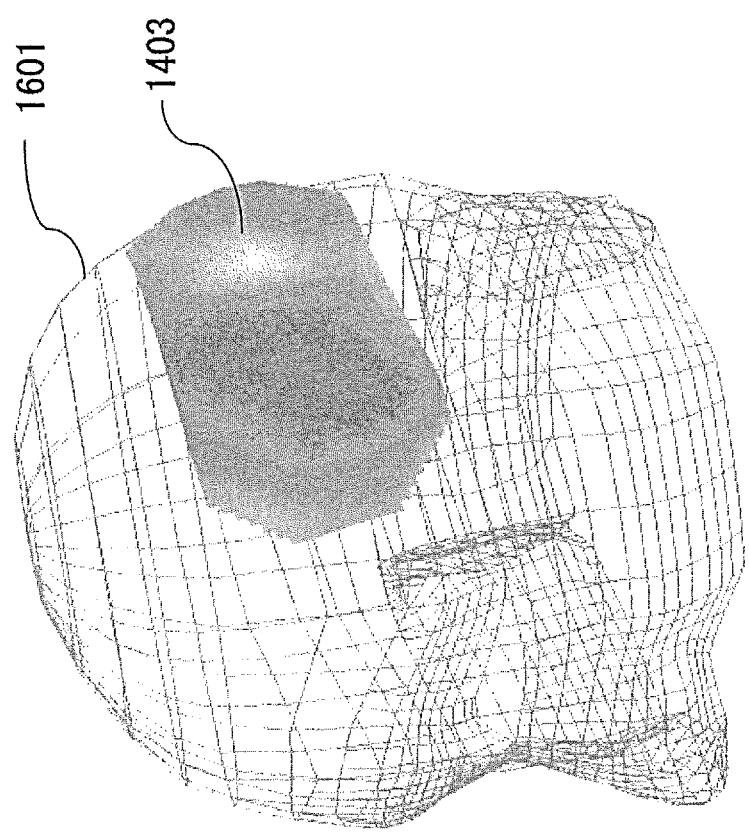
FIG. 22 is an explanatory diagram showing a superimposed image of the pseudo-morphological image (wire frame image) 1601 of an object and the living body optical measurement image 1403.

The signal processing unit 113 projects the tip positions of the optical fibers 106 and 109 calculated in Step 1205 using the calculated transmission parameter on a pseudo morphological image to calculate the position coordinate (Step 1507). Using the tip position coordinates of the optical fibers 106 and 109 on the pseudo morphological image, a living body optical measurement image is projected on the pseudo morphological image to create an image where the living body optical measurement image is superimposed on the pseudo morphological image (Step 1508). Hence, for example, as shown in FIG. 22, an image can be created in which the living body optical measurement image 1403 is superimposed on the pseudo morphological image (wire frame image) 1601.

Third Embodiment

In the third embodiment, the tip positions of the optical fibers 106 and 109 on a morphological image of an object such as an MRI image are displayed in real time while the optical fibers 106 and 109 are being applied to the object 107 after the optical fiber plug 204 is attached to the holder 108. This helps to determine attachment points of the optical fibers 106 and 109. Since the method where attachment points of the optical fibers on a morphological image of an object such as an MRI image are displayed in real time while the optical fibers 106 and 109 are being applied to the object 107 is a publicly known technique described in PTL 1, the overview will be described here, and points to which the measurement method of the present invention is applied in the process will be described hereinafter.

Figure 23:
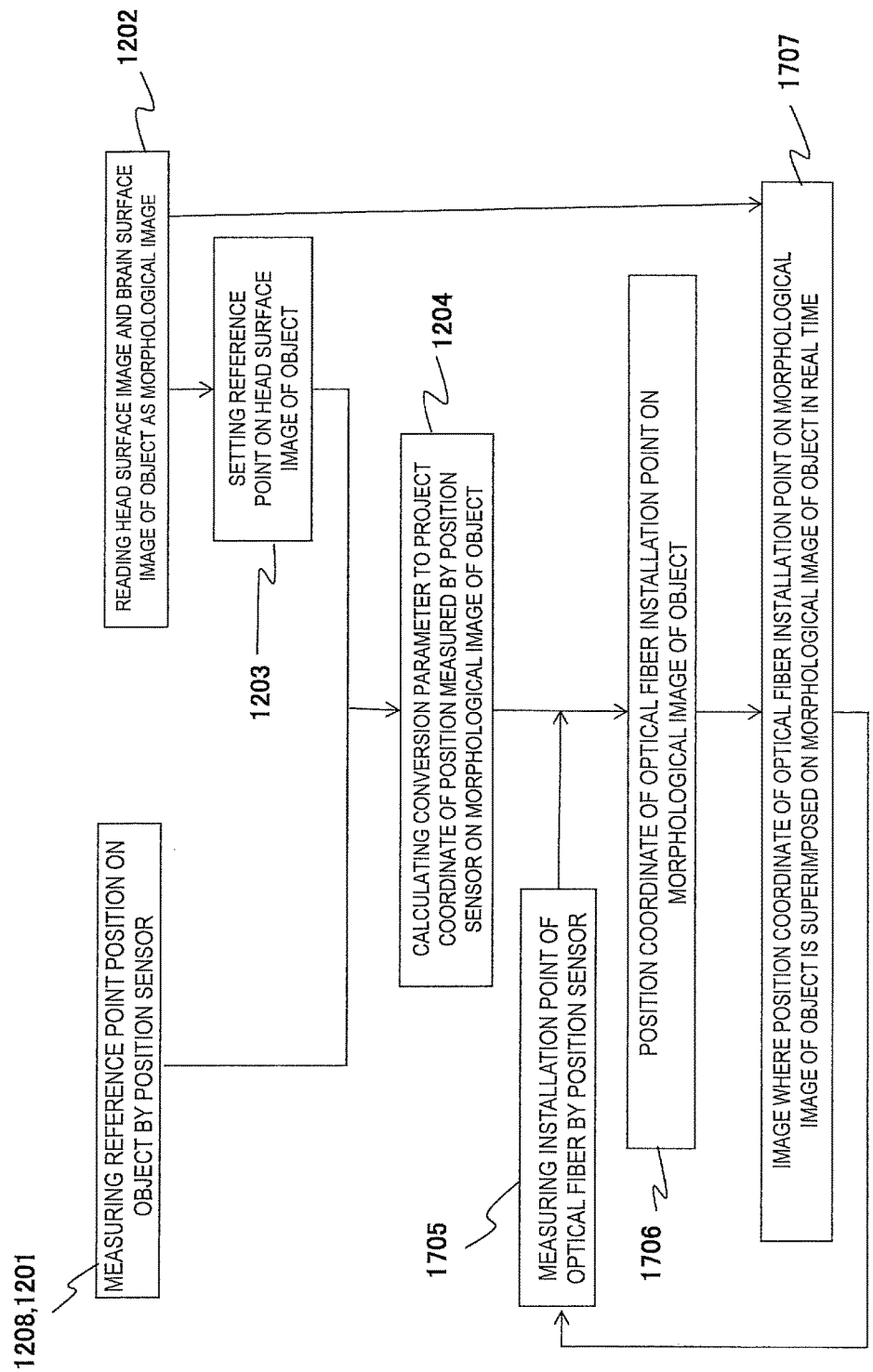
FIG. 23 is a flow chart showing a process of a living body optical measurement method of the third embodiment.

FIG. 23 is a flow chart that shows a flow for displaying attachment points of optical fibers on a morphological image in real time. Similarly to Steps 1208 and 1201 of the first embodiment, the mobile position sensor 118 is used to measure positions of the reference points on the object 107. However, although Steps 1208 and 1201 are performed after all the optical fiber plugs 204 are first attached to the holder 108 in the first embodiment, Steps 1208 and 1201 are performed to measure the reference points before the optical fiber plugs 204 are attached in the third embodiment.

Next, similarly to Steps 1202, 1203, and 1204 of the first embodiment, a morphological image (a head surface image and brain surface image of an object imaged by an MRI apparatus, a CT apparatus, etc.) imaged in advance is read to search for positions of the reference points, and a transmission parameter to project the reference points measured in Step 1201 onto the reference points of a morphological image of an object is calculated.

The optical fiber plug 204 is attached to the holder 108, similarly to Steps 1209 and 1205 of the first embodiment, the engaging member 502 is engaged with the attached optical fiber plug 204, and then the tip positions of the optical fibers 106 and 109 re measured by the mobile position sensor 118 (Step 1705). This measurement may be performed each time one of the optical fiber plugs 204 is attached or at once after some of the optical fiber plugs 204 are attached.

The measured tip positions of the optical fibers 106 and 109 are projected on a morphological image using a transmission parameter calculated in Step 1204 to calculate the position coordinate (Step 1706). The tip positions of the optical fibers 106 and 109 on the morphological image are displayed on the morphological image (Step 1707).

Figure 24:
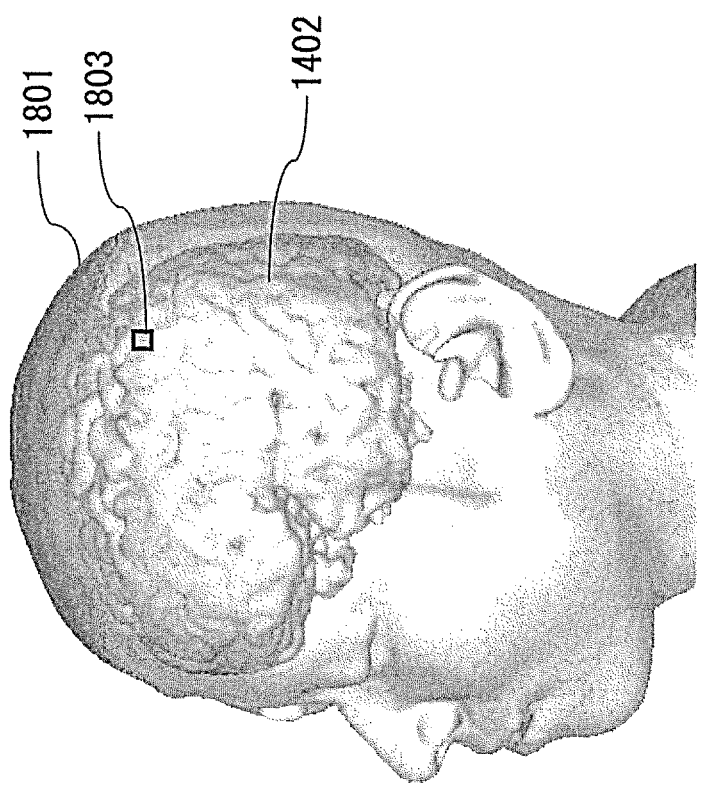
FIG. 24 is an explanatory diagram showing an image where the morphological image 1402 of an object and the tip position 1803 of the attached optical fiber are superimposed in real time.

Hence, for example, as shown in FIG. 24, the image 1801 is created and displayed in which the tip position 1803 of the optical fibers 106 and 109 is superimposed on the morphological image 1402. By repeating Steps 1705 to 1707 until all the optical fibers 106 and 109 are attached, positions of all the optical fibers 106 and 109 can be displayed on the morphological image 1402.

An operator can grasp where the attachment point of the optical fiber on a morphological image of an object is in real time. Therefore, the image 1801 helps to determine a position of the optical fiber to be attached on the object 107.

Because the tip positions of the optical fibers 106 and 109 can be measured by the mobile position sensor 118 without detaching the optical fiber plug 204 from the holder 108 in the present invention, positions of the attached optical fibers 106 and 109 can be displayed accurately. Also, because there is no need to detach the optical fiber plug 204 for position measurement, accuracy to display positions to which the optical fibers are attached in real time can be more enhanced.

Fourth Embodiment

In the fourth embodiment, similarly to the third embodiment, while the optical fibers 106 and 109 are being attached, the tip positions are displayed on a morphological image of the object 107 in real time. In addition to this, the tip positions of the optical fibers 106 and 109 for which a living body optical measurement was performed previously are also displayed so that an operator can grasp the positional relationship on the image.

There is a case where it is desirable to repeatedly perform a living body optical measurement for the same object 107 for the follow-up of the disease etc. with the optical fibers 106 and 109 attached to the same positions. However, because it is not easy to attach the optical fibers 106 and 109 so as to accurately correspond to the tip positions of the optical fibers 106 and 109 disposed previously, an image is created and displayed in which the previous positions of the optical fibers 106 and 109 and the positions of the optical fibers 106 and 109 that are currently being attached are displayed on a morphological image of an object such as an MRI image in real time in the present fourth embodiment, which helps to attach the optical fibers. Also, since creating such an image is a publicly known technique described in PTL 1, the overview will be described here, and points to which the measurement method of the present invention is applied in the process will be described hereinafter.

Figure 25:
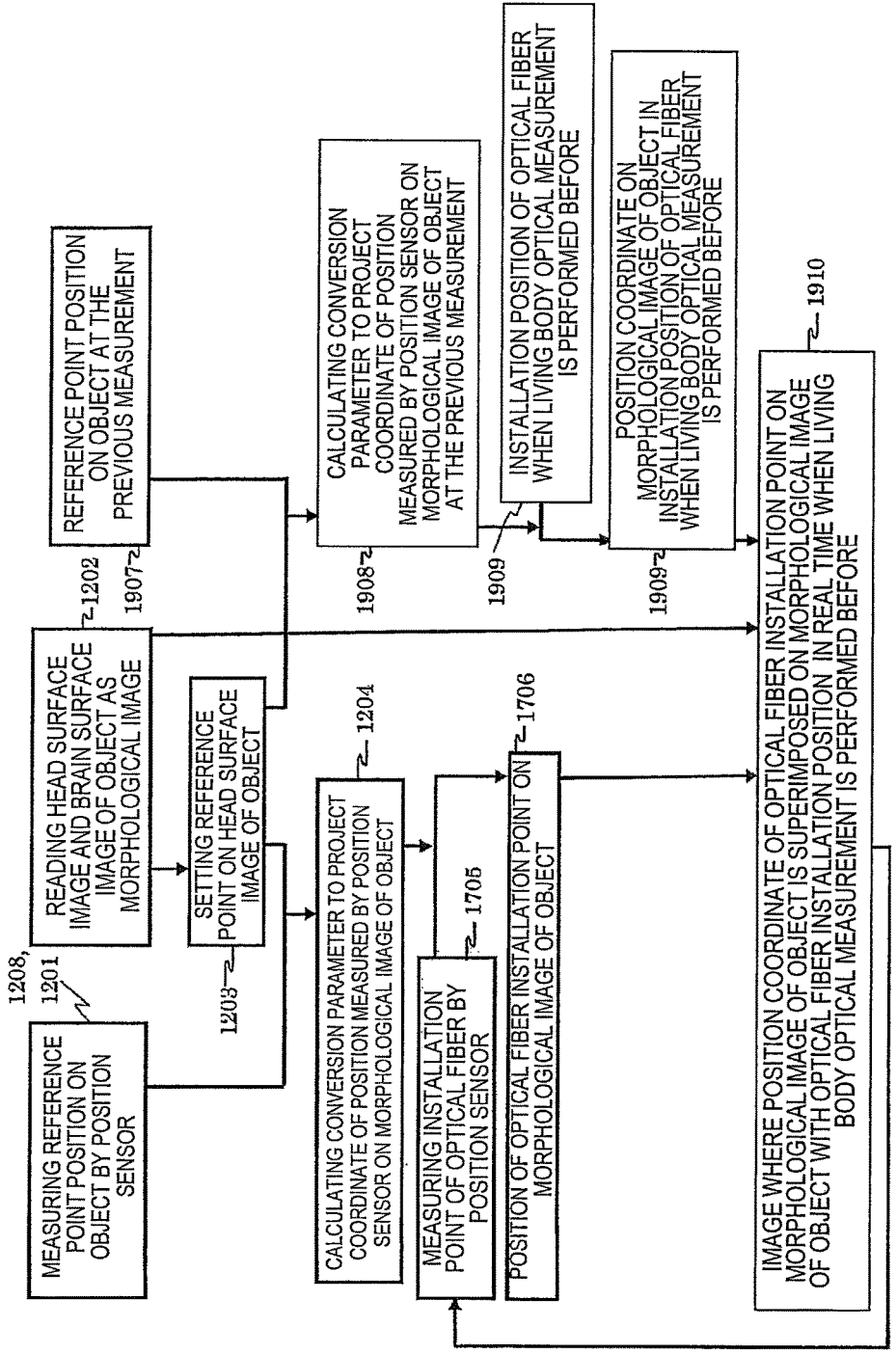
FIG. 25 is a flow chart showing a process of a living body optical measurement method of the fourth embodiment.

FIG. 25 is a flow chart showing a process of the present embodiment. Because Steps 1201 to 1204, 1208, 1705, and 1706 are similar to the third embodiment, the descriptions are omitted. Using these steps, position coordinates of the tip positions of the attached optical fibers 106 and 109 are searched on a morphological image of an object.

On the other hand, in Step 1907, positions of the reference points on the object 107 when they were measured previously are read from the storage unit 115, and then a transmission parameter for which the reference points are projected on a morphological image read in Step 1202 is calculated (Step 1908). This process is performed similarly to Step 1204.

The signal processing unit 103 loads the tip positions of the optical fibers 106 and 109 when they were measured previously from the storage unit 115, projects the tip positions on a morphological image using the calculated transmission parameter, and then calculates the position coordinate (Steps 1909 and 1909). This process can be performed similarly to Step 1706. The previous tip positions of the optical fibers 106 and 109 to be loaded from the storage unit 115 in Step 1909 may be those corresponding only to the optical fibers 106 and 109 measured in Step 1705 or may be loaded for all the optical fibers 106 and 109.

The tip positions searched in Step 1706 of the optical fibers 106 and 109 that are being attached currently and the previous positions of the optical fibers 106 and 109 are superimposed and displayed on a morphological image (Step 1910).

Figure 26:
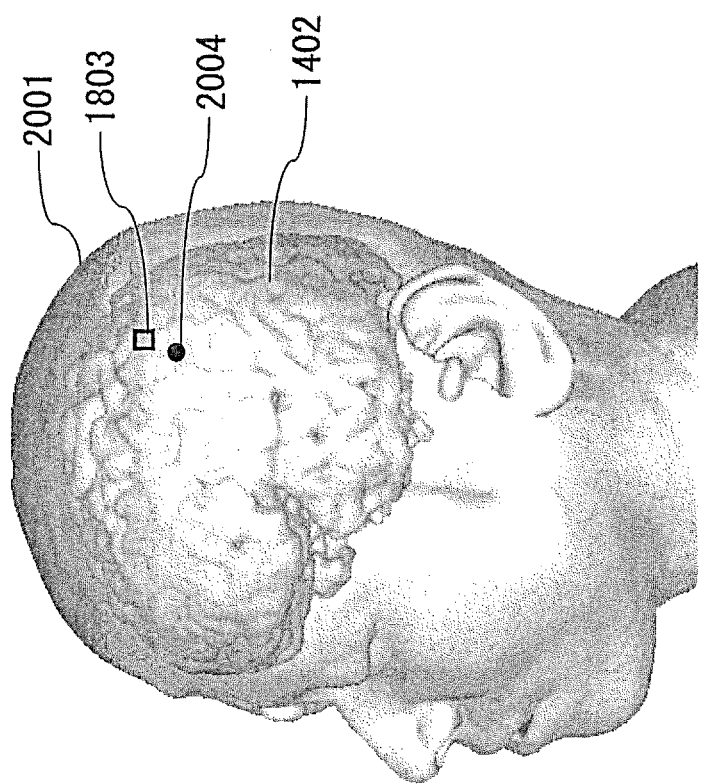
FIG. 26 is an explanatory diagram showing an image where the morphological image 1402 of an object, the tip position 1803 of the attached optical fiber, and the previous tip position 2004 of the optical fiber are superimposed in real time.

Hence, for example, as shown in FIG. 26, the image 1801 can be created and displayed for which the tip position 1803 of the optical fibers 106 and 109 that are being attached currently and the tip position 2004 that was measured previously of the optical fibers 106 and 109 are superimposed on the morphological image 1402. Therefore, an operator can grasp a positional relationship for whether attachment points of the optical fibers 106 and 109 for when a living body optical measurement was previously performed on the morphological image 1402 of an object correspond to positions of the optical fibers 106 and 109 that are being attached currently. If the positions are shifted each other, an operator can perform a correction such as re-attaching the optical fiber plug 204 by shifting the position of the holder 108. Therefore, a living body optical measurement can be performed by applying the optical fibers to positions corresponding to those of the optical fibers measured previously.

Figure 27:
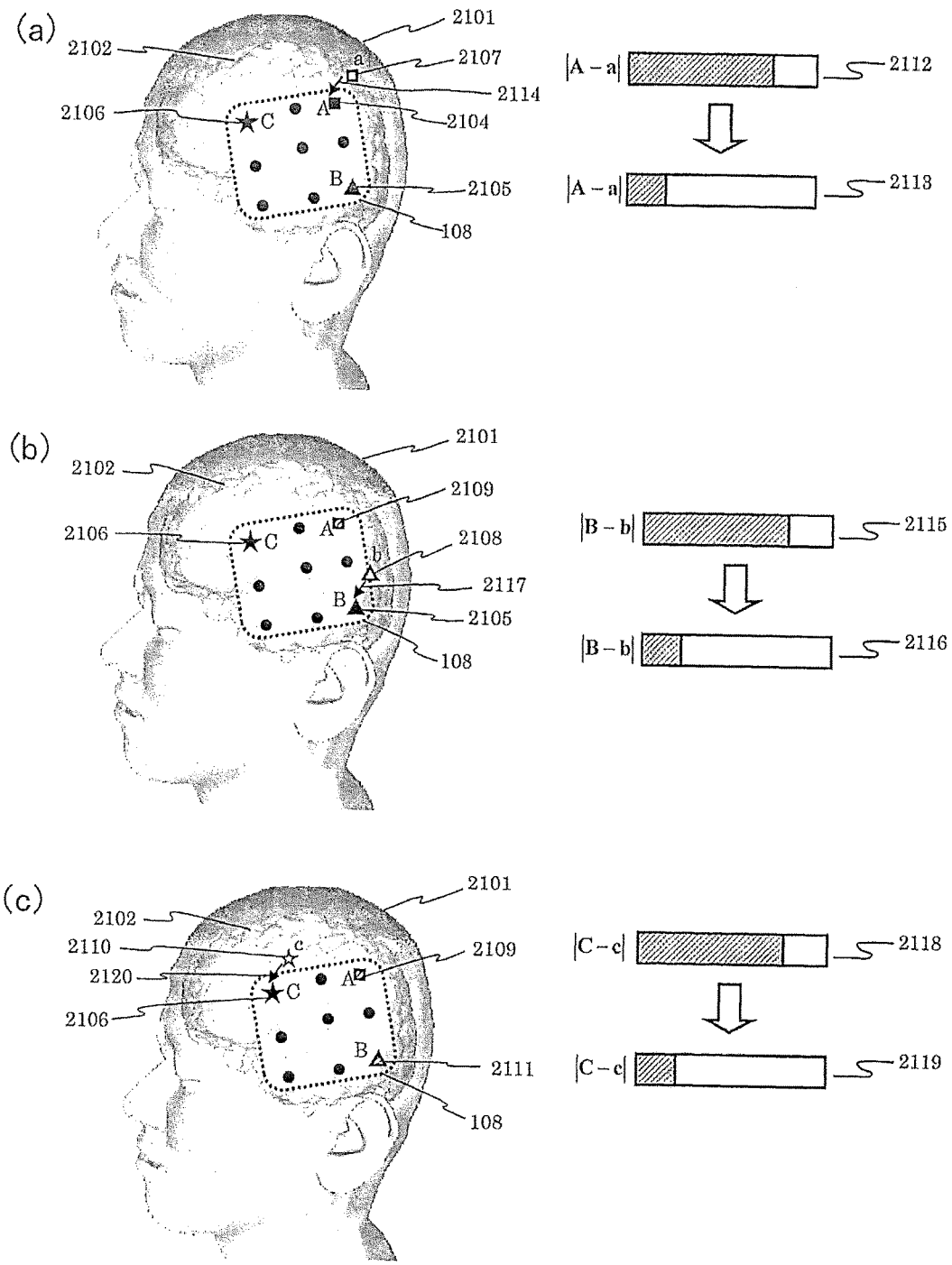
FIGS. 27(a), 27(b), and 27(c) are explanatory diagrams showing an image example to display error bars showing a shift amount and a moving direction so that positions of optical fibers in three locations correspond to the previous positions of the optical fibers one by one in order.

Here, how to adjust the tip positions of the optical fibers that are being attached currently to those of the optical fibers measured previously will be further described using FIGS. 27 and 28. In a living body optical measurement, because the optical fibers 106 and 109 are plural and held by the holder 108, the optical fibers 106 and 109 cannot be moved completely independent from each other. In the present embodiment, three attachment points of the optical fibers are adjusted to those for when a living body optical measurement was performed previously.

First, how to adjust the positions one by one is described using FIG. 27. As shown in FIG. 27(a), in addition to the head surface image 2101 and the brain surface image 2102 of an object, the position A (2104), the position B (2105), and the position C (2106) of the tips of the optical fibers for when a living body optical measurement was performed previously are displayed. Although the position of the holder 108 is not necessarily important and may not be displayed, the position of the holder 108 is shown here in the diagram for convenience of description.

The tip position a (2107) of the optical fiber attached first is displayed in real time. The position of the holder 108 is corrected so that the tip position a (2107) is adjusted to the position A (2104). Taking a coordinate value of the position a (2107) as a and a coordinate value of the position A (2104) as A, the signal processing unit 113 can display the error bars 2112 and 2113 with lengths proportional to |A-a| which is a gap between the position a (2107) and the position A (2104) in order to help attach the optical fiber. When the gap is large, the long error bar 2112 is displayed, and when the gap is small, the short error bar 2113 is displayed. Shifting the holder 108 by an operator so that the error bar is short can easily attach the first optical fiber to the position A (2104).

Also, it may be configured so that the signal processing unit 113 displays the arrow 2114 showing a direction of the vector A-a equivalent to an operating direction to correct an orientation of the gap on the display screen. Additionally, a beep sound may be generated at a volume proportional to a gap size |A-a| so that an operator can recognize a gap size even with a sound.

Next, how to attach the second optical fiber is shown in FIG. 27(b). The position b (2108) of the attachment point of the optical fiber that is being attached second is displayed in real time, and the optical fiber is attached so that the position b (2108) is adjusted to the position B (2105). At this time, the first optical fiber plug and the second optical fiber plug are connected by the holder 108. Therefore, while holding the first optical fiber attached already by hand so that it is not moved from the position A (2109), attachment is performed by shifting the holder 108 so that the position b (2108) of the optical fiber attached second corresponds to the previous position B (2105). At this time, similarly to when the first optical fiber is attached, in order to help attach the second optical fiber, the error bars 2115 and 2116 with lengths proportional to a gap size |B-b| between the position b (2108) and the position B (2105) can be displayed, the arrow 2117 showing a direction of the vector B-b equivalent to an operating direction to correct an orientation of the gap can be displayed, and a beep sound can be generated at a volume proportional to a gap size |B-b|.

Then, how to attach the third optical fiber is shown in FIG. 27(c). The position c (2110) of the attachment point of the optical fiber that is being attached third is displayed in real time, and the optical fiber is attached so that the position c (2110) is adjusted to the position C (2106). At this time, the first optical fiber plug, the second optical fiber plug, and the third optical fiber plug are connected by the holder. Therefore, while holding the first and second optical fibers attached already by hand so that they are not moved from the position A (2109) and the position B (2111), the third optical fiber is attached. Similarly, the error bars 2118 and 2119 with lengths proportional to a gap size |C-c| can be displayed, the arrow 2120 can be displayed, and a beep sound can be generated.

Hence, while an operator is helping to correct a position of an optical fiber, positions of the optical fiber being attached and the previous optical fiber can be displayed in real time.

Next, using FIG. 28, the method to simultaneously adjust the three positions of the optical fibers to the previous ones will be described.

FIG. 28 shows the current positions of the three optical fibers as the position a (2207), the position b (2208), and the position c (2209) in real time by measuring the positions simultaneously with the three mobile position sensors 118.

Because the current positions of the three optical fibers are shown, the optical fibers can be attached simultaneously without shifting the positions when the respective current positions are adjusted to the positions of the attached optical fibers in which a living body optical measurement was performed before. In this case, taking coordinate values of current positions a, b, and c (2207, 2208, and 2209) of the optical fibers as a, b, and c respectively as well as coordinate values of previous positions A, B, and C (2204, 2205, and 2206) of the optical fibers as A, B, and C, the error bars 2214, 2215, 2216, 2218, 2219, and 2220 with lengths that are proportional to |A-a|, |B-b|, and |C-c| can be displayed simultaneously as shifts in the respective positions in order to help attach the three optical fibers. Also, the arrows 2210, 2211, and 2212 that show the vectors A-a, B-b, and C-c can be displayed. Additionally, the error bars 2213 and 2217 with lengths proportional to (|A-a|+|B-b|+|C-c|)/3 as an average of the shifts in the attachment positions of the three optical fibers and the vector 2221 can also be displayed. A beep sound at a volume proportional to (|A-a|+|B-b|+|C-c|)/3 can also be generated.

Fifth Embodiment

Positions of the optical fibers are superimposed and displayed on a morphological image of an object measured by an MRI apparatus etc. in real time in the fourth embodiment. However, positions of the optical fibers are superimposed and displayed on a pseudo morphological image (wire frame image) of an object in real time in the fifth embodiment.

Figure 29:
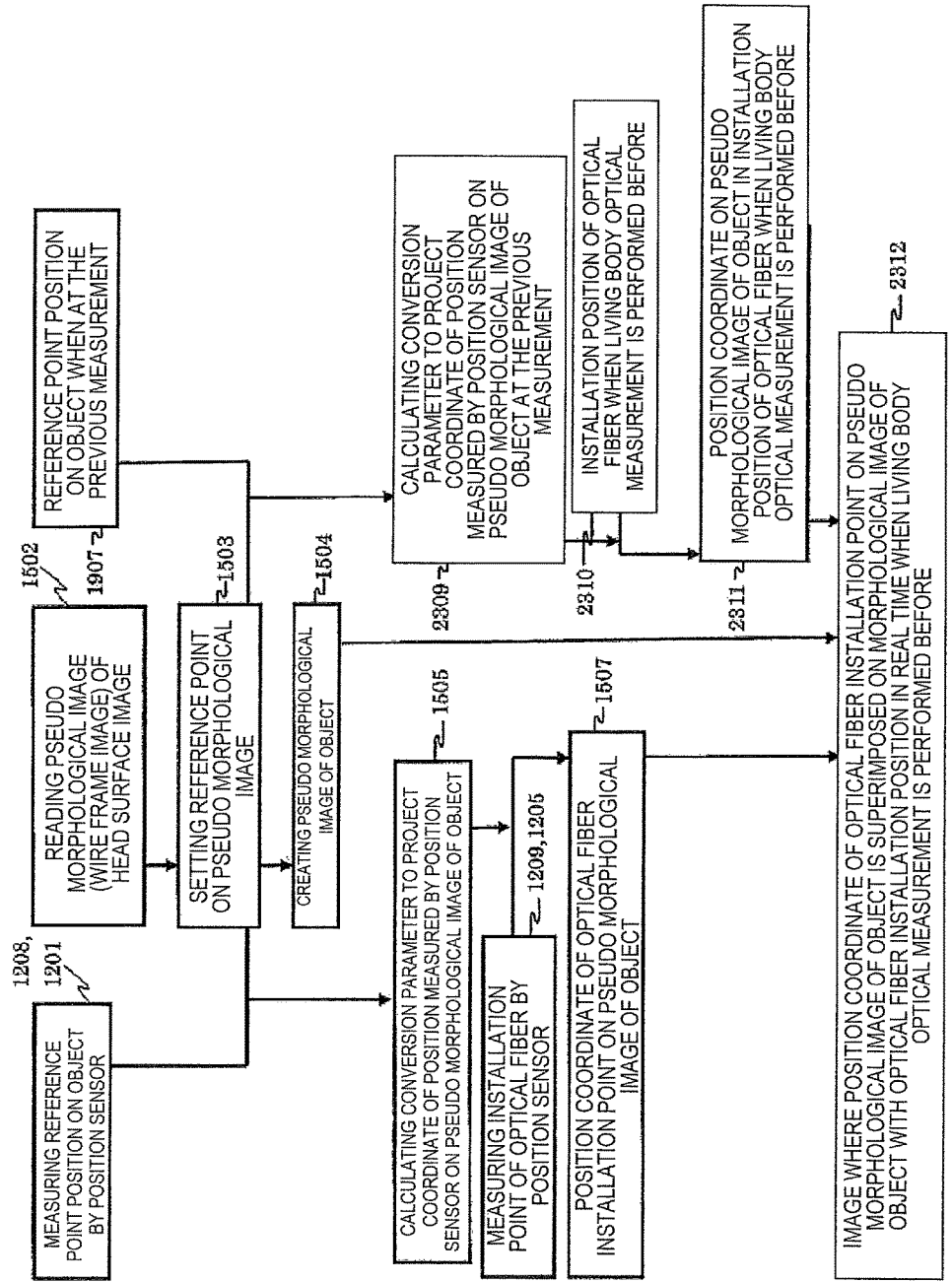
FIG. 29 is a flow chart showing a process of a living body optical measurement method of the fifth embodiment.

FIG. 29 is a flow chart showing a process of the fifth embodiment. Although Steps 1201, 1205, 1208, 1209, 1502 to 1505, and 1507 in the process of FIG. 29 are similar to those in FIG. 21 of the second embodiment, what is different from the second embodiment is to calculate position coordinates on a morphological image of an object in the tip positions of the optical fibers 106 and 109 currently being attached by these steps. These are similar to the third and fourth embodiments.

On the other hand, similarly to Step 1907 of the fourth embodiment, the positions of the reference points on the object 107 measured previously are loaded from the storage unit 115 to calculate a transmission parameter by which the reference points are projected on a pseudo morphological image read in Step 1503 (Step 2309). Also, similarly to Steps 1908 to 1909 of the fourth embodiment, the signal processing unit 113 loads the tip positions of the optical fibers 106 and 109 measured previously from the storage unit 115, projects the positions on a pseudo morphological image, and then calculates the position coordinates (Steps 2309 to 2311). What is different from the fourth embodiment is to perform projection on a pseudo morphological image in the fifth embodiment while projection is performed on a morphological image in the fourth embodiment.

The tip positions calculated in Step 1507 of the optical fibers 106 and 109 that are being attached currently and the previous positions of the optical fibers 106 and 109 are superimposed and displayed on a pseudo morphological image (Step 2312). Hence, the tip positions of the optical fibers that are being attached currently and the previous ones can be superimposed and displayed on a pseudo morphological image of an object in real time.

Figure 30:
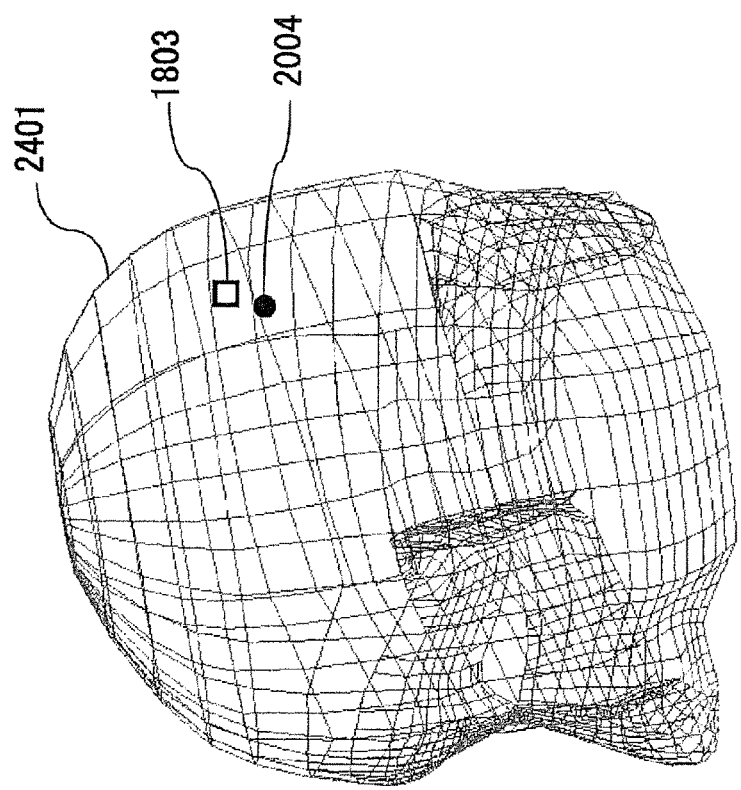
FIG. 30 is an explanatory diagram showing an image where the pseudo morphological image (wire frame image) 2401 of an object, the tip position 1803 of the attached optical fiber, and the previous tip position 2004 of the optical fiber are superimposed in real time.

As an example, an image where the tip position 1803 of the optical fiber that is being attached currently and the tip position 2004 of the optical fiber for which a living body optical measurement was performed previously are superimposed on the pseudo morphological image 2401 of an object in real time is shown in FIG. 30.

According to the embodiments of the present invention described above, the technical problems to be described below can be solved.

In clinical practice, an image of a living body optical measurement apparatus is superimposed on a head surface image and brain surface image as well as an X-ray CT image and MRI image, and it is desirable to superimpose both the images each other exactly at a high positional accuracy in order to perform diagnosis with the images.

Specifically, it is desirable to measure positions of optical fibers of a living body optical measurement apparatus with an accuracy of millimeters or less. In PTL 1, the tip of a mobile position sensor comes into contact with an attachment hole for an optical fiber of a probe holder, which detects the position.

However, the size of an attachment hole for an optical fiber of a probe holder is as large as approximately 1 to 2 cm, and because the probe holder is lifted up from the scalp by the hair, a contact position of the tip of the optical fiber and the scalp cannot be measured directly from a position of the attachment hole for the optical fiber of the probe holder. Also, individual differences are large in the size and the shape of the head of an object, and a distance from the probe holder and the scalp considerably depends on an amount of hair, the length, and how the hair grows. Therefore, it is also difficult to accurately presume a position of the tip of an optical fiber from a position of an attachment hole for an optical fiber of a probe holder.

On the other hand, an operation in which the tips of optical fibers are fixed to the scalp so that light can be detected from another optical fiber by irradiating light from an optical fiber to the scalp is very sensitive and requires patience because the head hair prevents the optical fibers from contacting the scalp. As a specific operation, first, a sheet-like probe holder is fixed to the head of an object with a belt etc., the tip of an optical fiber is contacted with the scalp while the head hair is being moved away with a thin stick, and then the optical fiber is fixed to the probe holder.

At this time, if the tip of an optical fiber is applied to the scalp too strongly, it is undesirable that an object feels pain, and if the tip of the optical fiber is up from the scalp conversely, noise enters into an optical signal, which cannot detect the optical signal. Therefore, it is required that the tip of the optical fiber contacts the scalp with an appropriate pressure. This operation is repeated for the number of the optical fibers (normally, 30 to 80 pieces). Additionally, if the tip position is shifted by 0.5 mm by a hand of an operator touching the optical fiber fixed once, measurement cannot be performed due to noise entering into an optical signal. Therefore, while close attention is being paid so as not to shift the tip position by touching the fixed optical fiber, the other optical fibers also need to be fixed. Additionally, cables are connected to the respective optical fibers, and even if the cables are pulled by touching it accidentally, the tip position of the optical fiber is shifted. Therefore, it is also required that the cables are not touched.

Thus, there is considerable difficulty in measuring a tip position of an optical fiber fixed by sensitive operations at an accuracy of millimeters or less using a mobile position sensor. In clinical practice, a tip position of an optical fiber is measured using a mobile position sensor in order to superimpose an image of a living body optical measurement apparatus on an X-ray CT image etc. as follows. In the procedure, an optical fiber fixed by paying close attention as described above is detached from a hole of a probe holder, a mobile position sensor is inserted in a position where there was the tip of the optical fiber before, the tip is contacted with the scalp to detect the position, and then the optical fiber is fixed to the original position again while head hair is being moved away with a stick. During this, the procedure must be performed so as not to touch an adjacent optical fiber and a cable. These operations are repeated for all the optical fibers (normally, 30 to 80 pieces) in order.

Therefore, the method where a position on the scalp to be contacted by an optical fiber is measured with a mobile position sensor requires much time to prepare for the measurement, which results in limiting the number of measurable objects to one or two per day. It takes much time to attach optical fibers to an object, which imposes a burden also on a patient. Also, an optical fiber is detached from a probe holder once, and a mobile position sensor is inserted in a position where there was the tip of the optical fiber originally to perform measurement. Therefore, the position where the optical fiber contacts the scalp cannot be measured directly, and an operator must measure the original tip position before the detachment based on presumption, which results in a state where accurate position measurement cannot be performed. According to the embodiments of the present invention, these problems can be solved.

DESCRIPTION OF REFERENCE NUMERALS

101: light irradiation unit, 102: light measuring unit, 103: signal processing unit, 104: semiconductor laser, 105: optical module, 106: optical fiber, 107: object, 108: holder, 109: optical fiber, 110: photoelectric conversion element, 111: lock-in amplifier module, 112: A/D converter, 113: signal processing unit, 114: display device, 115: storage unit, 116: input/output unit, 117: three-dimensional position measuring unit, 118: mobile position sensor, 119: magnetic field generating module, 120: magnetic field generating region, 202: belt (jaw band) 204: optical fiber plug, 306: optical fiber tip, 2502: left-side body portion, 2503: right-side body portion, 2504: opening portion, 2505: nut, 2506: button hole, 2507: window, 2508: slot, 2510: notch, 2511: opening, 2602: holding portion, 2603: tubular portion, 2604: male screw-shaped protrusion, 2605: spring, 2607: bar-shaped member, 2609: screw, 2112, 2113, 2115, 2116, 2118, 2119, and 2213 to 2220: error bar

The invention claimed is:

1. A living body optical measurement apparatus comprising:
    a light irradiator and light measuring instrument that irradiates light to an object to measure light passed through the object;
    a signal processor that processes measurement data of the light irradiator and light measuring instrument to create a living body optical measurement image; and
    a position measuring instrument that measures a position where the light irradiator and light measuring instrument irradiates light to an object and a position to extract light passing through from the object,
    wherein the light irradiator and light measuring instrument includes:
    plural optical fibers;
    plural optical fiber plugs attached to the plural optical fibers respectively; and
    a holder that is detachably fixed to a measurement site of the object and holds the plural optical fiber plugs,
    wherein the position measuring instrument is equipped with a mobile position sensor and an engaging member having a shape to enable detachable engagement between the mobile position sensor and the plural optical fiber plugs that are held by the holder, and
    wherein a window is opened on a side surface of the engaging member so as to enable an operator to check for a tip of the mobile position sensor contacting with the tips of the plural optical fiber plugs.

2. The living body optical measurement apparatus according to claim 1, comprising:
    a calculator that calculates tip positions of the plural optical fibers of the plural optical fiber plugs from a positional relationship between a position detected by the mobile position sensor with which the optical fiber plugs are engaged using the engaging member and the measurement site surface.

3. The living body optical measurement apparatus according to claim 1,
    wherein each of the plural optical fiber plugs include a fixing jig fixed to the plural optical fibers, and
    the engaging member has a structure where the tip of the mobile position sensor contacts an end of the fixing jig in a case where the engaging member is engaged with the optical fiber plug.

4. The living body optical measurement apparatus according to claim 3,
    wherein the fixing jig includes plural tubular portions fixed to plural optical fibers respectively and plural bar-shaped portions fixed at the ends of the plural tubular portions respectively, and
    the mobile position sensor contacts the respective ends of the plural bar-shaped portions to detect the respective positions.

5. The living body optical measurement apparatus according to claim 1, wherein the engaging member has an opening with a shape engaged with the outer periphery of the plural optical fiber plugs.

6. The living body optical measurement apparatus according to claim 2,
    wherein the engaging member has an opening with a shape engaged with the outer periphery of the plural optical fiber plugs,
    the opening of the engaging member is formed on an axis whose depth direction is the same as the axial direction of the mobile position sensor to hold the plural optical fibers of the plural optical fiber plugs inserted in the opening on the same axis as the axial direction of the mobile position sensor, and
    the calculator calculates a position distant by a distance specified by the positional relationship in the axial direction from the tip of the mobile position sensor as each tip position of the plural optical fibers.

7. The living body optical measurement apparatus according to claim 5,
    wherein the outer peripheries of the tips of the plural optical fibers are fixed to the respective fixing jigs of the plural optical fiber plugs, and the optical fibers are bent inside the plural optical fiber plugs and respectively pulled out from the side surfaces of the plural optical fiber plugs to the outsides, and a notch to insert an optical fiber pulled out of the side surface of the optical fiber plug is provided on an edge of the opening of the engaging member.

8. The living body optical measurement apparatus according to claim 1, wherein the plural optical fiber plugs include holding portions holding the respective fixing jigs movably to the axial direction of the tip of the optical fibers, the holder has plural holes to hold the plural optical fiber plugs respectively, and the outer peripheries of the holding portions of the plural optical fiber plugs have a shape engaged with the respective peripheral edges of the plural holes of the holder.

9. The living body optical measurement apparatus according to claim 1, wherein the position measuring instrument further includes a pseudo plug to be attached to the engaging member when a reference site of the object for which the optical fiber plug is not disposed is measured.

10. The living body optical measurement apparatus according to claim 9, wherein the signal processor displays a predetermined display prompting the operator to measure a reference site of the object on a display device after the pseudo plug is attached to the engaging member and loads position data of the reference site of the object measured by the position measuring instrument from the position measuring instrument, and the pseudo plug is detached from the engaging member, a predetermined display prompting an operator to measure tip positions of the plural optical fibers is displayed on the display device, the position data of the tips of the plural optical fibers measured by the position measuring instrument is loaded respectively from the position measuring instrument, and the loaded reference position and position information of the tip of the plural optical fibers are added to a living body optical measurement image.

11. The living body optical measurement apparatus according to claim 10, wherein the signal processor creates an image where the living body optical measurement image is superimposed on an image showing morphology of the object using the position information.

12. A living body optical measurement method that irradiates light to an object to measure the light passed through the object, comprising:

an optical fiber attachment process where the tips of plural optical fibers attached to the respective tips of plural optical fiber plugs are disposed so as to contact the object by a holder holding the plural optical fiber plus; and an optical fiber position detection process where an engaging member engages a mobile position sensor with the plural optical fiber plugs, and tip positions of the plural optical fibers are calculated from a positional relationship between a position detected by the mobile position sensor at that time and the surface of a measurement site, further including an operator visually checking for a tip of the mobile position sensor contacting with the tips of the plural optical fiber plugs through a window opened on a side surface of the engaging member.

13. The living body optical measurement method according to claim 12, further comprising:

a reference position detection process, wherein a pseudo plug is attached to the engaging member, the tip of the pseudo plug contacts a reference site of the object for which the optical fiber plug is not disposed, and then the reference position is calculated from a positional relationship between a position detected by the mobile position sensor at that time and the surface of the measurement site.

14. The living body optical measurement method according to claim 13, further comprising:

a pseudo plug attachment display process that displays a display prompting an operator to attach the pseudo plug to the engaging member on a display device before the reference position detection process.

* * * * *